(12) United States Patent
Huang

(10) Patent No.: US 10,485,803 B2
(45) Date of Patent: Nov. 26, 2019

(54) PYRIMIDINE COMPOUNDS AS JAK KINASE INHIBITORS

(71) Applicant: THERAVANCE BIOPHARMA R&D IP, LLC, South San Francisco, CA (US)

(72) Inventor: Xiaojun Huang, Sunnyvale, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

(21) Appl. No.: 16/014,233

(22) Filed: Jun. 21, 2018

(65) Prior Publication Data

US 2018/0303836 A1   Oct. 25, 2018

Related U.S. Application Data

(62) Division of application No. 15/498,803, filed on Apr. 27, 2017, now Pat. No. 10,028,960.

(60) Provisional application No. 62/328,737, filed on Apr. 28, 2016.

(51) Int. Cl.
| | |
|---|---|
| A61K 31/519 | (2006.01) |
| C07D 211/00 | (2006.01) |
| C07D 211/06 | (2006.01) |
| C07D 487/04 | (2006.01) |
| C07D 451/04 | (2006.01) |
| C07D 451/14 | (2006.01) |

(52) U.S. Cl.
CPC .......... *A61K 31/519* (2013.01); *C07D 211/00* (2013.01); *C07D 211/06* (2013.01); *C07D 451/04* (2013.01); *C07D 451/14* (2013.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 6,653,300 | B2 | 11/2003 | Bebbington et al. |
| 6,660,731 | B2 | 12/2003 | Bebbington et al. |
| 6,664,247 | B2 | 12/2003 | Bebbington et al. |
| 7,531,536 | B2 | 5/2009 | Bebbington et al. |
| 7,625,913 | B2 | 12/2009 | Bebbington et al. |
| 7,691,853 | B2 | 4/2010 | Bebbington et al. |
| 8,222,256 | B2 | 7/2012 | Zhang |
| 8,815,877 | B2 | 8/2014 | Aliagas-Martin et al. |
| 9,725,470 | B2 | 8/2017 | Hudson et al. |
| 10,028,960 | B2 * | 7/2018 | Hudson ................ A61K 31/519 |
| 2008/0004302 | A1 | 1/2008 | Theoclitou et al. |
| 2009/0312543 | A1 | 12/2009 | Bebbington et al. |
| 2016/0052930 | A1 | 2/2016 | Fensome et al. |
| 2016/0347772 | A1 | 12/2016 | Hudson et al. |

FOREIGN PATENT DOCUMENTS

| | | |
|---|---|---|
| WO | 2007059299 A1 | 5/2007 |
| WO | 2015/094803 A1 | 6/2015 |

OTHER PUBLICATIONS

Kozak et al.. "Discovery and Profiling of Novel, Intestinally-Restricted Oral pan-JAK Inhibitors for the Treatment of Inflammatory Bowel Diseases", Cambridge Healthtech Institute's 12th annual Conference Presentation, San Diego, Apr. 25, 2017.
International Search Report and the Written Opinion for PCT application No. PCT/US2017/029796 dated Jun. 14, 2017.

* cited by examiner

*Primary Examiner* — Golam M Shameem
(74) *Attorney, Agent, or Firm* — Jeffrey A. Hagenah; Florence Jovic

(57) ABSTRACT

The invention provides compounds of formula (I):

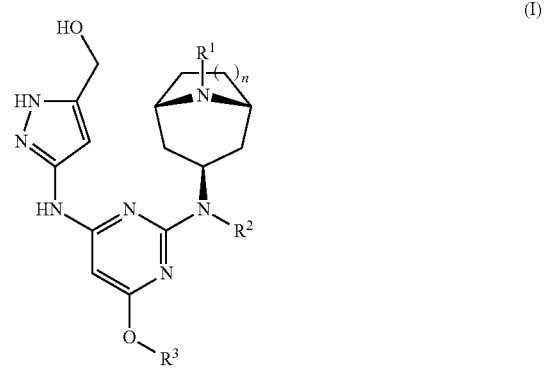

wherein the variables are defined in the specification, or a pharmaceutically-acceptable salt thereof, that are inhibitors of JAK kinases. The invention also provides pharmaceutical compositions comprising such compounds, methods of using such compounds to treat gastrointestinal and other inflammatory diseases, and processes and intermediates useful for preparing such compounds.

6 Claims, 4 Drawing Sheets

PYRIMIDINE COMPOUNDS AS JAK KINASE INHIBITORS

CROSS-REFERENCE TO RELATED APPLICATIONS

This application is a divisional application of U.S. Ser. No. 15/498,803, filed on Apr. 27, 2017, now allowed; which application claims the benefit of U.S. Provisional Application No. 62/328,737, filed on Apr. 28, 2016; the entire disclosures of which are incorporated herein by reference in their entirety.

BACKGROUND OF THE INVENTION

Field of the Invention

The invention is directed to pyrimidine compounds useful as JAK kinase inhibitors. The invention is also directed to pharmaceutical compositions comprising such compounds, methods of using such compounds to treat inflammatory diseases, and processes and intermediates useful for preparing such compounds.

State of the Art

Ulcerative colitis is a chronic inflammatory disease of the colon. The disease is characterized by inflammation and ulceration of the mucosal layer of the rectum and the large intestine. Common symptoms include diarrhea, bloody stools, and abdominal pain. The clinical course is intermittent, marked by alternating periods of exacerbation and remission. Incidence seems to be greater in developed than in developing countries. An estimated 1.2 million people in major industrialized countries suffer from ulcerative colitis and the numbers are expected to increase along with population growth. Patients with ulcerative colitis are at an increased risk of developing colorectal cancer. (e.g. Danese et al. *N Engl J Med,* 2011, 365, 1713-1725).

Although there exists a variety of therapeutic options to promote and maintain remission of ulcerative colitis (UC) in patients, none is ideal. Sulfasalazine-related treatments are often effective in mild UC, but much less so in moderate to severe disease. Corticosteroids are often used to provide rapid induction of remission in patients with moderate to severe UC. However, chronic use of steroids to maintain remission is discouraged due to their association with longer term adverse effects (e.g., osteoporosis and fractures, infections, cataracts, slower wound healing and suppression of adrenal gland hormone production). Systemic immunosuppressants such as azathioprine, cyclosporine and methotrexate have a slow onset and modest efficacy in moderate to severe UC patients, but prolonged use can be problematic due to consequences of long-term systemic immunosuppression (e.g., increased risk of infections and lymphoma). Anti-TNFα antibodies (e.g., infliximab and adalimumab), while expensive and requiring subcutaneous or intravenous administration, are efficacious in approximately 60 to 70% of UC patients with moderate to severe disease. However, up to one third of patients fail to respond adequately, while another third of initial responders develop tolerance over a few weeks (Allez et al., *J Crohn's Colitis,* 2010, 4, 355-366; Rutgeerts et al., *N Engl J Med,* 2005, 353, 2462-2476). The most recently approved UC therapy, vedolizumab, an anti-integrin $\alpha_4\beta_7$ antibody, is efficacious in moderate to severe UC patients although its parenteral route is suboptimal, and the consequences of long-term immunosuppression via this mechanism remain to be determined. Despite existing therapeutic options, about 10 to 20% of UC patients still require colectomy within 10 years of diagnosis (Targownik et al., *Am J Gastroenterol,* 2012, 107, 1228-1235). It is clear there remains an unmet medical need for an effective therapy to promote and maintain remission of moderate to severe UC without the safety concerns resulting from chronic, systemic immunosuppression.

While the mechanism underlying ulcerative colitis is not completely understood, it is believed that environmental factors in genetically susceptible individuals evoke an inappropriate (excessive) reaction by the immune system to gut microbiota, resulting in colonic inflammation, tissue damage, and the associated symptoms characteristic of the disease.

Although the precise pathogenesis of UC is unclear, it is apparent that proinflammatory cytokines play a pivotal role in the immunological response (Strober et al., *Gastroenterol,* 2011, 140, 1756-1767). Many of the proinflammatory cytokines most commonly elevated in UC (e.g., IL-4, IL-6, IL-13, IL-15, IL-23, IL-24, IFNγ and leptin), rely on the JAK family of tyrosine kinases (i.e., JAK1, JAK2, JAK3 and Tyk2) for signal transduction. Binding of a cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings.

Atopic dermatitis (AD) is a common chronic inflammatory skin disease that affects an estimated 14 million people in the United States alone. It is estimated that AD affects 10 to 20% of children and 1 to 3% of adults in developed countries (Bao et al., *JAK-STAT,* 2013, 2, e24137) and the prevalence is increasing. Elevation of proinflammatory cytokines that rely on the JAK-STAT pathway, in particular, IL-4, IL-5, IL-10, IL-12, IL-13, IFNγ, and TSLP has been associated with AD (Bao et al., Leung et al., *The Journal of Clinical Investigation,* 2004, 113, 651-657). In addition, upregulation of IL-31, another cytokine that signals through a JAK pairing, has been shown to have a role in the pruritis associated with the chronic state of AD (Sunkoly et al., *Journal of Allergy and Clinical Immunology,* 2006, 117, 411-417).

Inhibition of the family of JAK enzymes could inhibit signaling of many key pro-inflammatory cytokines. Thus JAK inhibitors are likely to be useful in the treatment of ulcerative colitis, and other gastrointestinal inflammatory diseases such as Crohn's disease and immune checkpoint inhibitor induced colitis, atopic dermatitis, and other inflammatory skin diseases, allergic rhinitis, asthma, and chronic obstructive pulmonary disease (COPD). However, due to the modulating effect of the JAK/STAT pathway on the immune system, systemic exposure to JAK inhibitors may have an adverse systemic immunosuppressive effect. It would be desirable, therefore, to provide new JAK inhibitors which have their effect at the site of action without significant systemic effects. In particular, for the treatment of gastrointestinal inflammatory diseases, such as ulcerative colitis, it would be desirable to provide new JAK inhibitors which can be administered orally and achieve therapeutically relevant exposure in the gastrointestinal tract with minimal systemic exposure. It would also be desirable to provide new JAK inhibitors for the treatment of atopic dermatitis, which can be administered topically with minimal systemic exposure.

SUMMARY OF THE INVENTION

In one aspect, the invention provides novel compounds having activity as JAK kinase inhibitors.

Accordingly, the invention provides a compound of formula (I):

(I)

wherein
$R^1$ is selected from:
(a) —S(O)$_2$R$^4$, wherein R$^4$ is selected from:
C$_{1-4}$alkyl, wherein C$_{1-4}$alkyl is optionally substituted with —CN, —OC$_{1-3}$alkyl, or C$_{3-6}$cycloalkyl,
heterocyclyl containing 4 to 6 ring atoms including one nitrogen atom, wherein any heterocyclyl is optionally substituted with —CN, C$_{3-6}$cycloalkyl, pyridinyl, wherein pyridinyl is optionally substituted with fluoro, and phenyl;

(b) C$_{1-4}$alkyl, wherein C$_{1-4}$alkyl is optionally substituted with —CN, or
pyridinyl, wherein pyridinyl is optionally substituted with —CN; and
(c) —C(O)R$^5$, wherein R$^5$ is selected from:
C$_{1-4}$alkyl, wherein C$_{1-4}$alkyl is optionally substituted with C$_{3-6}$cycloalkyl, or with one or two fluoro,
—OC$_{1-4}$alkyl,
C$_{3-6}$cycloalkyl, and
morpholinyl;
$R^2$ is hydrogen or methyl;
$R^3$ is C$_{1-3}$alkyl; and
n is 1 or 2;
or a pharmaceutically-acceptable salt or stereoisomer thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated.

The invention also provides a pharmaceutical composition comprising a compound of the invention and a pharmaceutically-acceptable carrier.

In another aspect, the invention provides a particular compound of formula (I) in crystalline free base form. Crystalline 1-(((1R,3s,5S)-3-((4-((5-(hydroxymethyl)-1H-pyrazol-3-yl)amino)-6-methoxypyrimidin-2-yl)(methyl) amino)-9-azabicyclo[3.3.1]nonan-9-yl)sulfonyl)azetidine-3-carbonitrile has been found to have a melting temperature in the range of about 235° C. to about 245° C., typically between about 237° C. and about 242° C., and to exhibit weight changes of less than about 0.4% when exposed to a range of relative humidity between about 5% and about 90% at room temperature.

The invention also provides a method of treating gastrointestinal inflammatory disease, in particular, ulcerative colitis, in a mammal, the method comprising administering to the mammal a compound or a pharmaceutical composition of the invention.

In yet another method aspect, the invention provides a method of treating inflammatory diseases or disorders of the skin, in particular atopic dermatitis, in a mammal, the method comprising applying a compound or a pharmaceutical composition of the invention to the skin of the mammal.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating gastrointestinal inflammatory disease in a mammal. The invention further provides the use of a compound of the invention in the manufacture of a formulation or medicament for treating inflammatory diseases of the skin.

BRIEF DESCRIPTION OF THE DRAWINGS

Various aspects of the present invention are illustrated by reference to the accompanying drawings.

DETAILED DESCRIPTION OF THE INVENTION

Figure 1:
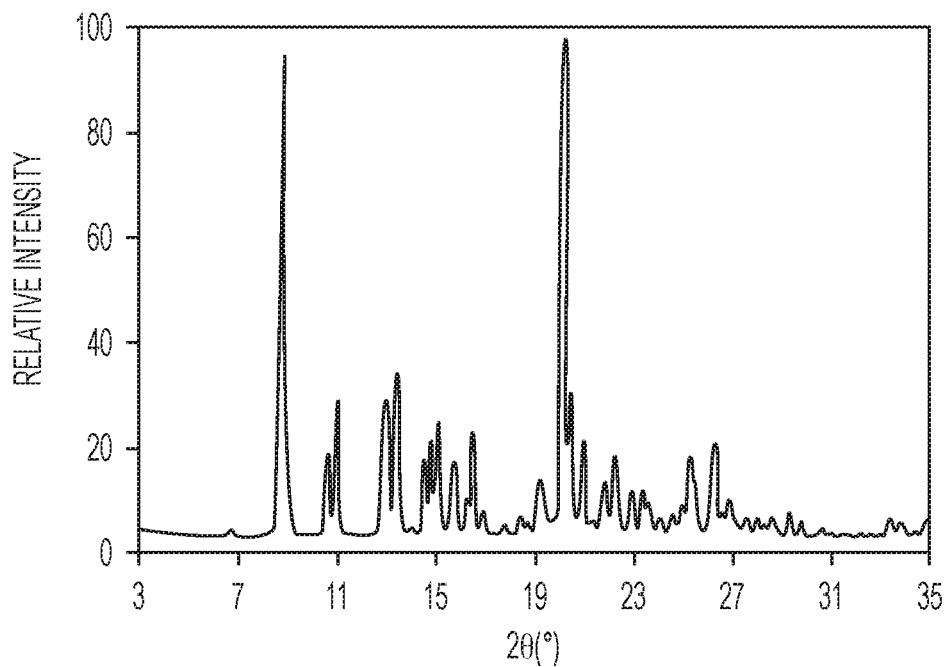
FIG. 1 shows a powder x-ray diffraction (PXRD) pattern of crystalline Form I 1-(((1R,3s,5S)-3-((4-((5-(hydroxymethyl)-1H-pyrazol-3-yl)amino)-6-methoxypyrimidin-2-yl) (methyl)amino)-9-azabicyclo[3.3.1]nonan-9-yl)sulfonyl) azetidine-3-carbonitrile [hereinafter Form I].

Among other aspects, the invention provides JAK kinase inhibitors of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In one aspect of the invention, $R^1$ is selected from (a) —S(O)$_2$R$^4$, wherein R$^4$ is selected from C$_{1-4}$alkyl, wherein C$_{1-4}$alkyl is optionally substituted with —CN, —OC$_{1-3}$alkyl, or C$_{3-6}$cycloalkyl; heterocyclyl containing 4 to 6 ring atoms including one nitrogen atom, wherein any heterocyclyl is optionally substituted with —CN; C$_{3-6}$cycloalkyl; pyridinyl, wherein pyridinyl is optionally substituted with fluoro; and phenyl; (b) C$_{1-4}$alkyl, wherein C$_{1-4}$alkyl is optionally substituted with —CN,

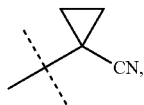

or pyridinyl, wherein pyridinyl is optionally substituted with —CN; and (c) C(O)R$^5$, wherein R$^5$ is selected from C$_{1-4}$alkyl, wherein C$_{1-4}$alkyl is optionally substituted with C$_{3-6}$cycloalkyl, or with one or two fluoro; —OC$_{1-4}$alkyl; C$_{3-6}$cycloalkyl; and morpholinyl.

In another aspect R$^1$ is —S(O)$_2$R$^4$, wherein R$^4$ is selected from C$_{1-4}$alkyl, wherein C$_{1-4}$alkyl is optionally substituted with —CN, —OC$_{1-3}$alkyl, or C$_{3-6}$cycloalkyl; heterocyclyl containing 4 to 6 ring atoms including one nitrogen atom wherein any heterocyclyl is optionally substituted with —CN; C$_{3-6}$cycloalkyl; pyridinyl, wherein pyridinyl is optionally substituted with fluoro; and phenyl.

In yet another aspect, R$^1$ is —S(O)$_2$R$^4$, wherein R$^4$ is selected from C$_{1-2}$alkyl, wherein C$_{1-2}$alkyl is optionally substituted with —CN, —OCH$_3$, or cyclopropyl; azetidinyl, wherein azetidinyl is optionally substituted with —CN; pyrrolidinyl; cyclopropyl; pyridinyl, wherein pyridinyl is optionally substituted with fluoro; and phenyl.

In still another aspect, R$^1$ is —S(O)$_2$R$^4$, wherein R$^4$ is methyl, ethyl, azetidinyl, pyrrolidinyl, cyclopropyl, pyridinyl, or phenyl, wherein ethyl is optionally substituted with methoxy, azetidinyl is optionally substituted with —CN, and pyridinyl is optionally substituted with fluoro.

In one aspect, R$^1$ is C$_{1-4}$alkyl, wherein C$_{1-4}$alkyl is optionally substituted with —CN,

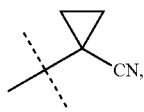

or pyridinyl, wherein pyridinyl is optionally substituted with —CN.

In another aspect, R$^1$ is C$_{1-2}$alkyl, wherein C$_{1-2}$alkyl is optionally substituted with —CN,

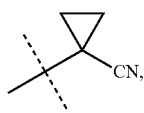

or pyridinyl, wherein pyridinyl is optionally substituted with —CN.

In one aspect, R$^1$ is —C(O)R$^5$, wherein R$^5$ is selected from C$_{1-4}$alkyl, wherein C$_{1-4}$alkyl is optionally substituted with C$_{3-6}$cycloalkyl, or with one or two fluoro; —OC$_{1-4}$alkyl; C$_{3-6}$cycloalkyl; and morpholinyl.

In another aspect, R$^1$ is —C(O)R$^5$, wherein R$^5$ is selected from C$_{1-2}$alkyl, wherein C$_{1-2}$alkyl is optionally substituted with cyclopropyl, or with one or two fluoro; —OC$_{1-4}$alkyl; C$_{3-6}$cycloalkyl; and morpholinyl.

In yet another aspect, R$^1$ is —C(O)R$^5$, wherein R$^5$ is —CHF$_2$, —CH$_2$-cyclopropyl, —OCH$_3$, —O-isobutyl, cyclobutyl, cyclopentyl, or morpholinyl.

In one aspect R$^2$ is hydrogen or methyl. In a specific aspect R$^2$ is methyl.

In one aspect, R$^3$ is C$_{1-3}$alkyl.

In another aspect, R$^3$ is methyl.

In one aspect, n is 1 or 2. In another aspect, n is 2.

In a certain aspect, the invention provides compounds of formula (II):

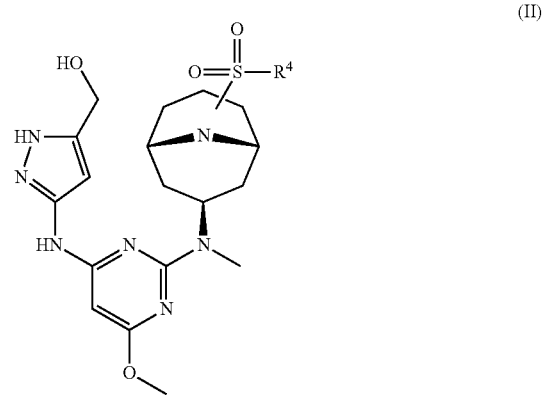

wherein the variable R$^4$ is as defined herein.

In one aspect, the invention provides the compounds of Examples 1-9 and Tables 1-3 below.

In another aspect, the invention provides a compound selected from:
1-(((1R,3s,5S)-3-((4-((5-(hydroxymethyl)-1H-pyrazol-3-yl)amino)-6-methoxypyrimidin-2-yl)(methyl)amino)-8-azabicyclo[3.2.1]octan-8-yl)sulfonyl)azetidine-3-carbonitrile,
1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile,
(3-((6-methoxy-2-(methyl((1R,3s,5S)-9-(methylsulfonyl)-9-azabicyclo[3.3.1]nonan-3-yl)amino)pyrimidin-4-yl)amino)-1H-pyrazol-5-yl)methanol,
(3-((6-methoxy-2-(((1R,3s,5S)-9-((2-methoxyethyl)sulfonyl)-9-azabicyclo[3.3.1]nonan-3-yl)(methyl)amino)pyrimidin-4-yl)amino)-1H-pyrazol-5-yl)methanol,
3-((1R,3s,5S)-3-((4-((5-(hydroxymethyl)-1H-pyrazol-3-yl)amino)-6-methoxypyrimidin-2-yl)(methyl)amino)-8-azabicyclo[3.2.1]octan-8-yl)propanenitrile,
5-(((1R,3s,5S)-3-((4-((5-(hydroxymethyl)-1H-pyrazol-3-yl)amino)-6-methoxypyrimidin-2-yl)amino)-9-azabicyclo[3.3.1]nonan-9-yl)methyl)picolinonitrile,
5-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)methyl)nicotinonitrile, isobutyl (1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonane-9-carboxylate, 2,2-difluoro-1-((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)ethan-1-one, (3-((2-(((1R,3s,5S)-9-(azetidin-1-ylsulfonyl)-9-azabicyclo[3.3.1]nonan-3-yl)amino)-6-methoxypyrimidin-4-yl)amino)-1H-pyrazol-5-yl)methanol, 1-(((1R,3s,5S)-3-((4-((5-(hydroxymethyl)-1H-pyrazol-3-yl)amino)-6-methoxypyrimidin-2-yl)amino)-9-azabicyclo[3.3.1]nonan-9-yl)sulfonyl)azetidine-3-carbonitrile, (3-((2-(((1R,3s,5S)-9-((5-fluoropyridin-3-yl)sulfonyl)-9-azabicyclo[3.3.1]nonan-3-yl)amino)-6-methoxypyrimidin-4-yl)amino)-1H-pyrazol-5-yl)methanol, (3-((6-methoxy-2-(((1R,3s,5S)-9-(phenylsulfonyl)-9-azabicyclo[3.3.1]nonan-3-yl)amino)pyrimidin-4-yl)amino)-1H-pyrazol-5-yl)methanol, (3-((2-(((1R,3s,5S)-9-(ethylsulfonyl)-9-azabicyclo[3.3.1]nonan-3-yl)amino)-6-methoxypyrimidin-4-yl)amino)-1H-pyrazol-5-yl)methanol, (3-((2-(((1R,3s,5S)-9-((cyclopropylmethyl)sulfonyl)-9-azabicyclo[3.3.1]nonan-3-yl)amino)-6-methoxypyrimidin-4-yl)amino)-1H-pyrazol-5-yl)methanol, (3-((6-methoxy-2-(((1R,3s,5S)-9-(pyridin-3-ylsulfonyl)-9-azabicyclo[3.3.1]nonan-3-yl)amino)pyrimidin-4-yl)amino)-1H-pyrazol-5-yl)methanol, 3-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)-sulfonyl)propanenitrile, (3-((6-methoxy-2-(methyl((1R,3s,5S)-9-(pyrrolidin-1-ylsulfonyl)-9-azabicyclo[3.3.1]nonan-3-yl)amino)pyrimidin-4-yl)amino)-1H-pyrazol-5-yl)methanol, (3-((2-(((1R,3s,5S)-9-(cyclopropylsulfonyl)-9-azabicyclo[3.3.1]nonan-3-yl)(methyl)amino)-6-methoxypyrimidin-4-yl)amino)-1H-pyrazol-5-yl)methanol, (3-((6-methoxy-2-(methyl((1R,3s,5S)-9-(pyridin-3-ylsulfonyl)-9-azabicyclo[3.3.1]nonan-3-yl)amino)pyrimidin-4-yl)amino)-1H-pyrazol-5-yl)methanol, (3-((6-methoxy-2-(methyl((1R,3s,5S)-9-(phenylsulfonyl)-9-azabicyclo[3.3.1]nonan-3-yl)amino)pyrimidin-4-yl)amino)-1H-pyrazol-5-yl)methanol, (3-((2-(((1R,3s,5S)-9-(azetidin-1-ylsulfonyl)-9-azabicyclo[3.3.1]nonan-3-yl)(methyl)amino)-6-methoxypyrimidin-4-yl)amino)-1H-pyrazol-5-yl)methanol, (3-((2-(((1R,3s,5S)-9-((cyclopropylmethyl)sulfonyl)-9-azabicyclo[3.3.1]nonan-3-yl)(methyl)amino)-6-methoxypyrimidin-4-yl)amino)-1H-pyrazol-5-yl)methanol, (3-((2-(((1R,3s,5S)-9-((5-fluoropyridin-3-yl)sulfonyl)-9-azabicyclo[3.3.1]nonan-3-yl)(methyl)amino)-6-methoxypyrimidin-4-yl)amino)-1H-pyrazol-5-yl)methanol, 4-(((1R,3s,5S)-3-((4-((5-(hydroxymethyl)-1H-pyrazol-3-yl)amino)-6-methoxypyrimidin-2-yl)amino)-9-azabicyclo[3.3.1]nonan-9-yl)methyl)picolinonitrile, (3-((6-methoxy-2-(((1R,3s,5S)-9-(pyridin-3-ylmethyl)-9-azabicyclo[3.3.1]nonan-3-yl)amino)pyrimidin-4-yl)amino)-1H-pyrazol-5-yl)methanol, 3-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)propanenitrile, 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)methyl)cyclopropane-1-carbonitrile, (3-((6-methoxy-2-(methyl((1R,3s,5S)-9-(pyridin-4-ylmethyl)-9-azabicyclo[3.3.1]nonan-3-yl)amino)pyrimidin-4-yl)amino)-1H-pyrazol-5-yl)methanol, 4-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)methyl)picolinonitrile, 2,2-difluoro-1-((1R,3s,5S)-3-((4-((5-(hydroxymethyl)-1H-pyrazol-3-yl)amino)-6-methoxypyrimidin-2-yl)amino)-9-azabicyclo[3.3.1]nonan-9-yl)ethan-1-one, isobutyl (1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonane-9-carboxylate, methyl (1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonane-9-carboxylate, ((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)(morpholino)methanone, 2-cyclopropyl-1-((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)ethan-1-one, cyclopentyl((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)methanone, and cyclobutyl((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)methanone, and pharmaceutically acceptable salts thereof.

Chemical structures are named herein according to IUPAC conventions as implemented in ChemDraw software (PerkinElmer, Inc., Cambridge, Mass.). For example, the compound of Example 2:

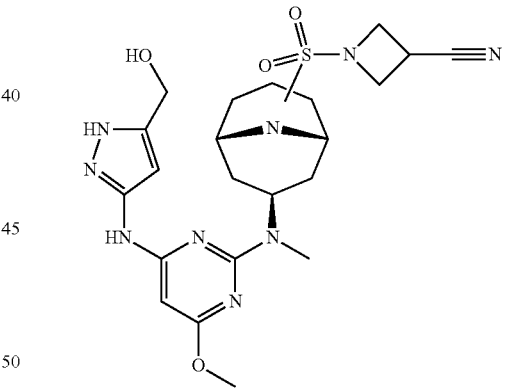

is designated as 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile. The (1R,3s,5S) notation describes the exo orientation of the pyrimidinylamino group with respect to the 9-azabicyclo[3.3.1]nonane group and similarly for the compounds containing an 8-azabicyclo[3.2.1]group (i.e. variable n=1). All of the compounds of the invention are in the exo orientation.

Furthermore, the pyrazolyl moiety of the compounds of formula (I) exists in tautomeric form. For example, the compound of Example 2 may equivalently be represented as:

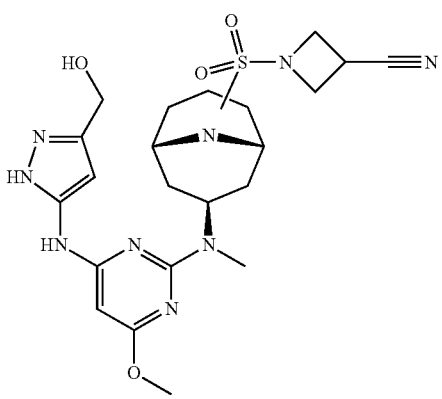

According to the IUPAC convention, these representations give rise to different numbering of the atoms of the pyrazolyl portion. The above representation is designated 1-(((1R,3s,5S)-3-((4-((3-(hydroxymethyl)-1H-pyrazol-5-yl)amino)-6-methoxypyrimidin-2-yl)(methyl)amino)-9-azabicyclo[3.3.1]nonan-9-yl)sulfonyl)azetidine-3-carbonitrile, where the underlining identifies where the name differs from that of the first representation. It will be understood that although structures are shown, or named, in a particular form, the invention also includes the tautomer thereof.

The compounds of the invention contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where an atom has been replaced or enriched with an atom having the same atomic number but an atomic mass different from the atomic mass that predominates in nature. Examples of isotopes that may be incorporated into a compound of formula (I) include, but are not limited to, $^{2}H$, $^{3}H$, $^{11}C$, $^{13}C$, $^{14}C$, $^{13}N$, $^{15}N$, $^{15}O$, $^{17}O$, $^{18}O$, $^{35}S$, and $^{18}F$. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocyclyl", "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), triisopropylsiliyl (TIPS), tert-butyldimethylsilyl (TBS or TBDMS), [2-(trimethylsilyl)-ethoxy]methyl (SEM); and the like. Numerous protecting groups, and their introduction and removal, are described in T. W. Greene and P. G. M. Wuts, Protecting Groups in Organic Synthesis, Third Edition, Wiley, New York General Synthetic Procedures Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials known to those skilled in the art. In particular, it will be appreciated that compounds of the invention may be prepared by a variety of process routes in which reactants are combined in different orders to provide different intermediates en route to producing final products.

A general method of preparing final compounds of the invention utilizes a key intermediate 1 as illustrated in Scheme 1. The variables $R^1$, $R^2$, $R^4$, $R^5$, and n are defined as in formula (I), $R^4$ represents an optionally substituted $C_{1-4}$alkyl, and L is a leaving group. The scheme shows compounds in which the variable $R^3$ is methyl. Compounds in which $R^3$ is $C_{2-3}$alkyl may be prepared analogously.

Scheme 1

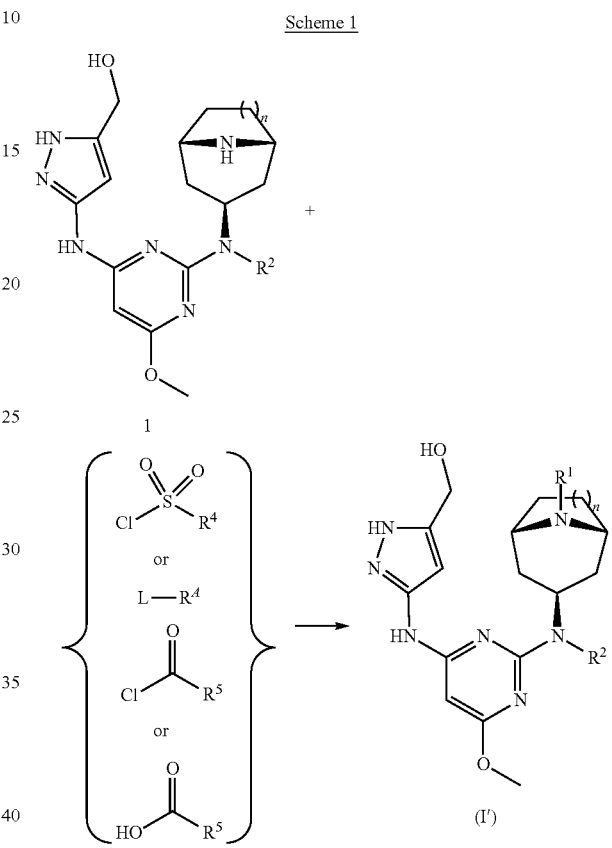

Sulfonamide compounds in which $R^1$ is defined as —S(O)$_2$ $R^4$ as in option (a) are typically prepared by contacting intermediate 1 with between about 1 and about 1.1 equivalents of a sulfonylchloride of the form Cl—S(O)$_2$ $R^4$ in the presence of an excess of base at a temperature on the order of 0° C. The reaction is typically conducted for between about 1 and about 24 hours or until the reaction is substantially complete.

To prepare compounds in which $R^1$ is an optionally substituted alkyl group as defined in option (b), the alkylation reaction typically uses a halo leaving group L, principally chloro or bromo. The reaction is typically conducted by contacting intermediate 1 with an excess of the reagent L-$R^4$ in an inert diluent in the presence of an excess of base. The reaction is typically conducted at a temperature between about 20° C. and about 60° C. for between about 10 and about 24 hours or until the reaction is substantially complete.

Alternatively, the Michael addition reaction may be used to prepare compounds in which $R^1$ is a cyanoethyl group. For example, as described in the examples below, to prepare a compound in which $R^1$ is —(CH$_2$)$_2$CN, intermediate 1 is contacted with between about 1 and about 1.5 equivalents of acrylonitrile in the presence of an excess of base, for example diisopropylethylamine or diazobicycloundecene.

The reaction is typically conducted at room temperature for between about 3 and about 24 hours or until the reaction is substantially complete.

Compounds in which $R^1$ is defined as —C(O)$R^5$ may be prepared using a carbonyl chloride of the form Cl—C(O)$R^5$, specifically a chloroformate when $R^5$ is defined as —O$C_{1-4}$ alkyl. Typically, intermediate 1 is contacted with about one equivalent of the carbonyl chloride in the presence of an excess of base at a temperature on the order of 0° C. The reaction is typically conducted for between about 1 and about 3 hours or until the reaction is substantially complete.

Alternatively, compounds in which $R^1$ is defined as —C(O)$R^5$ may be prepared by contacting intermediate 1 with a modest excess of carboxylic acid reagent HO—C(O)—$R^5$ under typical amide coupling conditions. The reaction is typically performed in the presence of an excess of base utilizing an activating agent such as N,N,N',N'-tetramethyl-O-(7-azabenzotriazol-1-yl)uronium hexafluorophosphate (HATU). The reaction is typically conducted at room temperature for between about 3 and about 24 hours or until the reaction is substantially complete.

An exemplary reaction for the preparation of intermediate 1 in which the variable $R^3$ is methyl is illustrated in Scheme 2.

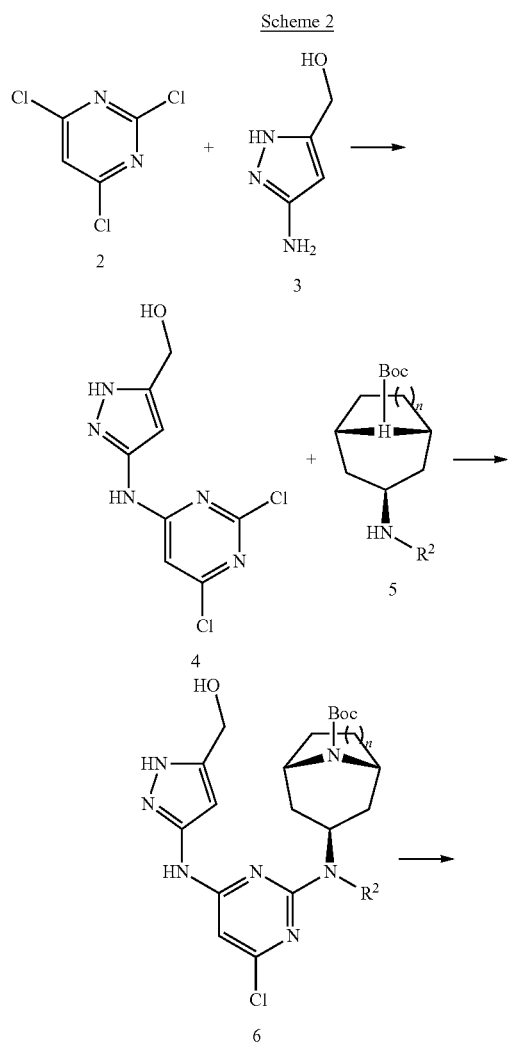

Scheme 2

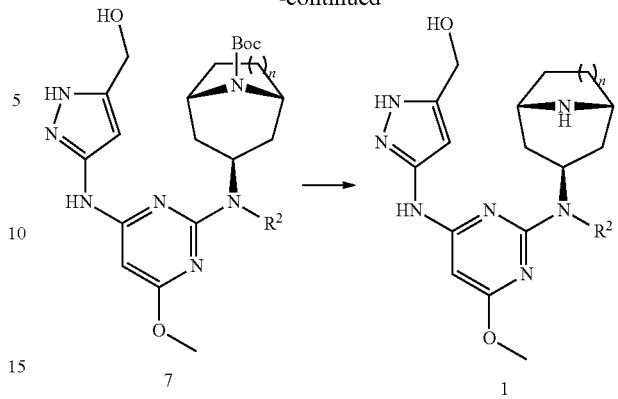

In the aromatic substitution reaction of step 1, the trichloropyrimidine 2 is reacted with an excess of the aminopyrazole-methanol intermediate 3 in the presence of base to provide intermediate 4. The Boc-protected amino-aza-bicyclo intermediate 5 is then reacted with intermediate 4 to provide intermediate 6. For example, intermediate 4 is combined with between about 1 and about 1.5 equivalents of the aza-bicyclo intermediate 5 in the presence of an excess of base, such as diisopropylethylamine. The reaction is typically conducted at elevated temperature, between about 85° C. and about 120° C. for between about 6 and about 12 hours or until the reaction is substantially complete. Reaction of intermediate 6 with sodium methoxide provides intermediate 7. The reaction is typically conducted in a sealed tube at elevated temperature, between about 85° C. and about 120° C. for between about 4 and about 10 hours or until the reaction is substantially complete. In the last step, the Boc group may be removed by standard treatment with an acid, typically hydrochloric acid, to provide intermediate 1.

Alternatively, intermediate 1 may be prepared by the sequence of steps illustrated in Scheme 3.

Scheme 3

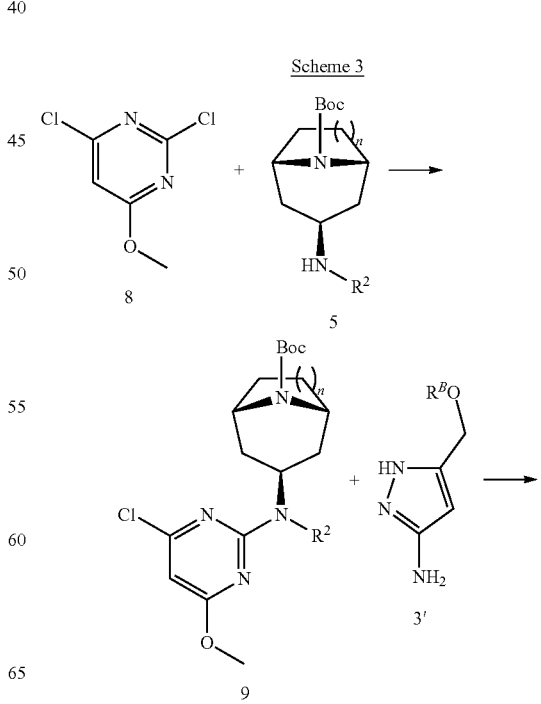

-continued

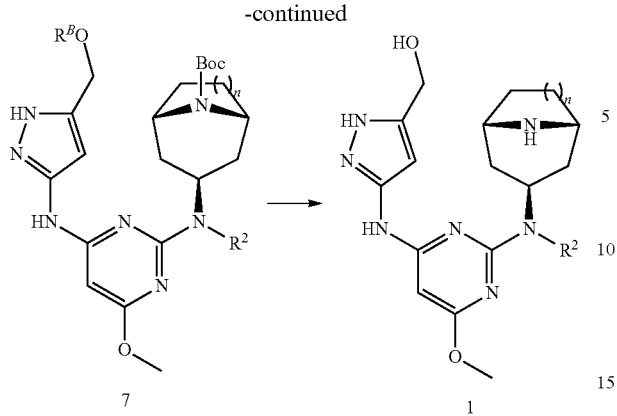

where $R^B$ is hydrogen or a silyl oxygen-protecting group, such as triisopropylsilyl (TIPS) or tert-butyldimethylsilyl (TBS). The Boc-protected amino-aza-bicylo group 5 is combined with the dichloro-methoxypyrimidine intermediate 8 to form intermediate 9. The reaction is typically conducted at elevated temperature in the presence of base. Intermediate 9 is then reacted with amino-pyrazole intermediate 3' under standard Buchwald conditions to provide intermediate 7. For example, intermediate 9 is combined with between about 1 and about 1.5 equivalents of the pyrazole intermediate 3' in the presence of a base such as cesium carbonate or potassium carbonate and a palladium catalyst. The reaction is typically conducted at elevated temperature, between about 80° C. and about 110° C., for between about 8 and about 24 hours or until the reaction is substantially complete. In the final step, the Boc protecting group is removed as in Scheme 2. When $R^B$ is a silyl protecting group, the silyl and Boc groups can be removed simultaneously.

Accordingly, in a method aspect, the invention provides a method for preparing a compound of formula (I) or a pharmaceutically acceptable salt thereof, the method comprising:

reacting a compound of formula (III):

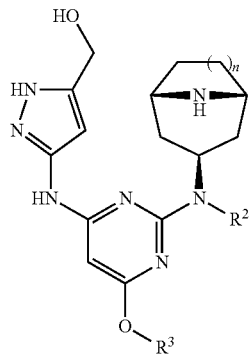

(III)

with
(i) Cl—S(O)$_2$R$^4$,
(ii) a compound of formula L-R$^4$ wherein L is a leaving group and R$^4$ is C$_{1-4}$alkyl, wherein C$_{1-4}$alkyl is optionally substituted with —CN,

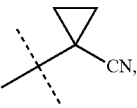

or pyridinyl, wherein pyridinyl is optionally substituted with —CN;
(iii) Cl—C(O)R$^5$, or
(iv) HO—C(O)R$^5$ wherein R$^1$, R$^2$, R$^3$, R$^4$, R$^5$, and n are as defined above, and optionally forming a pharmaceutically-acceptable salt to provide a compound of formula (I) or a pharmaceutically acceptable salt thereof.

In separate and distinct aspects, the invention provides a compound of formula (III) wherein the variables take any of the values described above and a compound of formula (III) wherein R$^2$ and R$^3$ are each methyl and n is 1 or 2.

In another method aspect, the invention provides a method for preparing a compound of formula 1

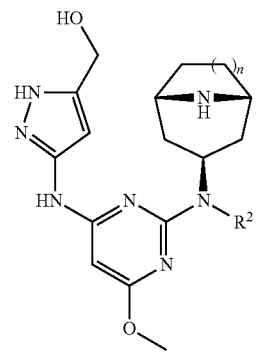

1 wherein R$^2$ and n are as defined above, the method comprising:

(a) reacting a compound of formula 9:

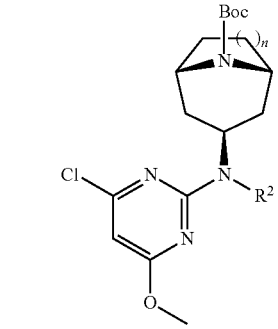

9 with a compound of formula 3:

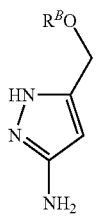

wherein $R^B$ is hydrogen or a silyl oxygen-protecting group to form a compound of formula 7:

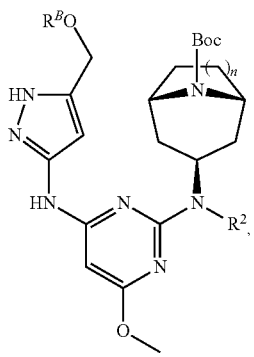

and (b) removing the protecting group or groups from the compound of formula 7 to provide the compound of formula 1.

Crystalline Forms

In another aspect, the invention provides 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile (see Examples 2 and 10-13) in crystalline freebase Form I and Form II.

In one aspect, crystalline freebase Form I is characterized by a powder X-ray diffraction (PXRD) pattern having significant diffraction peaks, among other peaks, at 2θ values of 8.89±0.20, 12.99±0.20, 13.44±0.20, and 20.16±0.20. Form I may be further characterized by a PXRD pattern having two or more additional diffraction peaks, including three or more and four or more additional diffraction peaks at 2θ values selected from 10.64±0.20, 10.99±0.20, 15.02±0.20, 15.74±0.20, 16.47±0.20, 20.93±0.20, 22.22±0.20, and 26.25±0.20. In another aspect, Form I is characterized by a PXRD pattern having diffraction peaks at 2θ values of 8.89±0.20, 10.64±0.20, 10.99±0.20, 12.99±0.20, 13.44±0.20, 15.02±0.20, 15.74±0.20, 16.47±0.20, 20.16±0.20, 20.93±0.20, 22.22±0.20, and 26.25±0.20.

As is well known in the field of powder X-ray diffraction, peak positions of PXRD patterns are relatively less sensitive to experimental details, such as details of sample preparation and instrument geometry, than are the relative peak heights. Thus, in one aspect, the crystalline Form I is characterized by a powder X-ray diffraction pattern in which the peak positions are substantially in accordance with those shown in FIG. 1.

In another aspect, crystalline Form I is characterized by its behavior when exposed to high temperature. As demonstrated in FIG. 2, the differential scanning calorimetry (DSC) trace recorded at a heating rate of 10° C. per minute exhibits a peak in endothermic heat flow, identified as a melt transition, in the range of about 235° C. to about 245° C., including between about 237° C. and about 242° C. The thermal gravimetric analysis (TGA) trace of FIG. 3 exhibits an onset of weight loss corresponding to post-melting decomposition.

Crystalline Form I has been demonstrated to have a reversible sorption/desorption profile with an exceptionally small propensity for hygroscopicity. Form I demonstrated less than about 0.4% weight gain in the humidity range of 5% to 90% relative humidity. No hysteresis was observed in two cycles of sorption and desorption. Form I is considered to be non-hygroscopic.

In addition, crystalline Form I has been demonstrated to be stable to micronization. No difference could be observed between the powder X-ray diffraction pattern of material that had not been micronized and the pattern of material of Form I after micronization.

Figure 5:
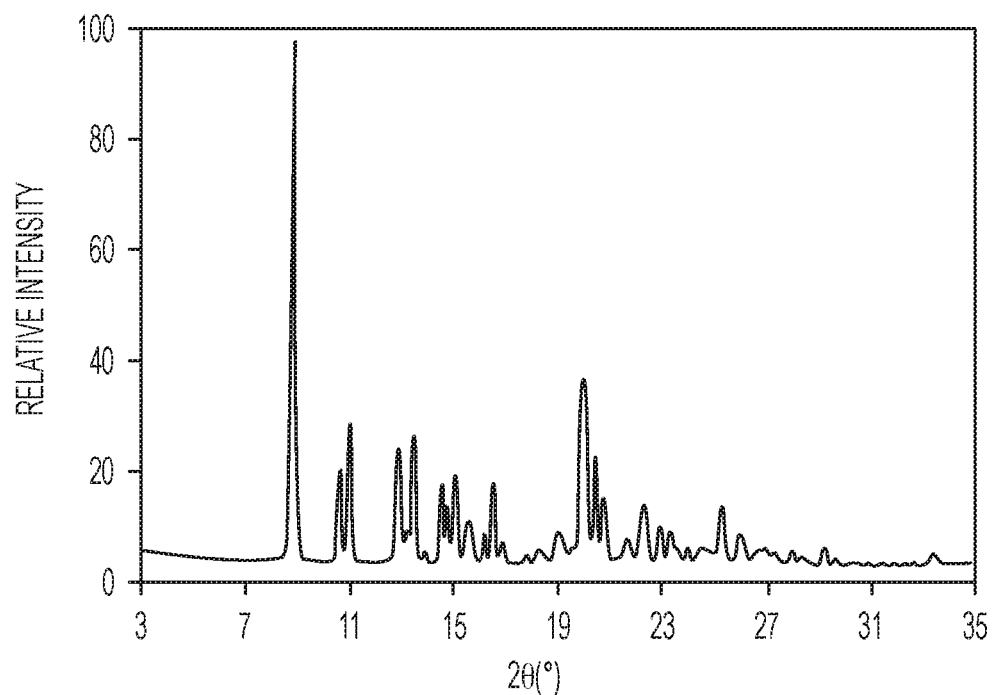
FIG. 5 shows a powder X-ray diffraction (PXRD) pattern of crystalline Form II 1-(((1R,3s,5S)-3-((4-((5-(hydroxymethyl)-1H-pyrazol-3-yl)amino)-6-methoxypyrimidin-2-yl) (methyl)amino)-9-azabicyclo[3.3.1]nonan-9-yl)sulfonyl) azetidine-3-carbonitrile [hereinafter Form II].

Crystalline freebase Form II is characterized by the PXRD pattern of FIG. 5 and further by its behavior when exposed to high temperature. As demonstrated in FIG. 6, the differential scanning calorimetry (DSC) trace recorded at a heating rate of 10° C. per minute exhibits a broad peak in endothermic heat flow in the range of about 205° C. to about 240° C., which, together with the thermal gravimetric analysis (TGA) trace of FIG. 7, may be interpreted as a merged melting transition and decomposition. Form II is a slightly hygroscopic solid which demonstrated small hysteresis between two cycles of sorption and desorption. Form II demonstrated about 1.2% weight gain in the humidity range of 5% to 90% relative humidity.

As described in Examples 11 and 12, Form I may be prepared by dissolving the compound in N-methylpyrrolidone (NMP) or dimethylformamide (DMF) and adding acetone and water as antisolvents in a ratio of about 1:1.5 to 1:1.75 acetone:water. The resulting reaction mixture is stirred for between about 4 hours and about 24 hours, filtered, washed with a mixture of acetone and water, such as a 1:1.4 mixture of acetone and water, and dried to provide crystalline Form I. A process for preparing crystalline Form II is described in Example 13.

In another aspect, the invention provides a method of preparing crystalline Form I, the method comprising: (a) dissolving 1-(((1R,3s,5S)-3-((4-((5-(hydroxymethyl)-1H-pyrazol-3-yl)amino)-6-methoxypyrimidin-2-yl)(methyl) amino)-9-azabicyclo[3.3.1]nonan-9-yl)sulfonyl)azetidine-3-carbonitrile in a diluent selected from N-methylpyrrolidone and dimethylformamide to form a reaction mixture; (b) adding acetone and water to the reaction mixture; and (c) isolating crystalline Form I from the reaction mixture.

Pharmaceutical Compositions

The compounds of the invention and pharmaceutically-acceptable salts thereof are typically used in the form of a pharmaceutical composition or formulation. Such pharmaceutical compositions may be administered to a patient by any acceptable route of administration including, but not limited to, oral, topical (including transdermal), rectal, nasal, inhaled, and parenteral modes of administration.

Accordingly, in one of its composition aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formula (II) and pharmaceutically-acceptable salts thereof.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; including from about 5 to about 70% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methylcellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethyleneglycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention may also be formulated for topical administration to the skin as an ointment or cream. Ointment formulations are semisolid preparations having a base of an oily or greasy material that is typically clear. Suitable oily materials for use in ointment formulations include petrolatum (petroleum jelly), beeswax, cocoa butter, shea butter, and cetyl alcohol. Ointments may optionally additionally include emollients and penetration enhancers, if desired.

Cream formulations may be prepared as emulsions comprising an oil phase and aqueous phase, typically including purified water. Components of cream formulations may include: oil bases, such as petrolatrum, mineral oils, vegetable and animal oils, and triglycerides; cream bases, such as lanolin alcohols, stearic acid, and cetostearyl alcohol; a gel base, such as polyvinyl alcohol; solvents, such as, propylene glycol and polyethylene glycol; emulsifiers, such as polysorbates, stearates, such as glyceryl stearate, octylhydroxystearate, polyoxyl stearate, PEG stearyl ethers, isopropyl palmitate, and sorbitan monostearate; stabilizers, such as polysaccharides and sodium sulfite; emollients (i.e. moisturizers), such as medium chain triglycerides, isopropyl myristate, and dimethicone; stiffening agents, such as cetyl alcohol and stearyl alcohol; antimicrobial agents, such as methylparaben, propylparaben, phenoxyethanol, sorbic acid, diazolidinyl urea, and butylated hydroxyanisole; penetration enhancers, such as N-methylpyrrolidone, propylene glycol, polyethylene glycol monolaurate, and the like; and chelating agents, such as edetate disodium.

The following non-limiting examples illustrate representative pharmaceutical compositions of the present invention.

Tablet Oral Solid Dosage Form

A compound of the invention or a pharmaceutically-acceptable salt thereof is dry blended with microcrystalline cellulose, polyvinyl pyrrolidone, and croscarmellose sodium in a ratio of 4:5:1:1 and compressed into tablets to provide a unit dosage of, for example, 5 mg, 20 mg or 40 mg active agent per tablet.

Capsule Oral Solid Dosage Form

A compound of the invention or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Liquid Formulation

A liquid formulation comprising a compound of the invention (0.1%), water (98.9%) and ascorbic acid (1.0%) is formed by adding a compound of the invention to a mixture of water and ascorbic acid.

Enteric Coated Oral Dosage Form

A compound of the invention is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Ointment Formulation for Topical Administration

A compound of the invention is combined with petrolatum, $C_8$-$C_{10}$ triglyceride, octylhydroxystearate, and N-methylpyrrolidone in a ratio to provide a composition containing 0.05% to 5% active agent by weight.

Ointment Formulation for Topical Administration

A compound of the invention is combined with white petrolatum, propylene glycol, mono- and di-glycerides, paraffin, butylated hydroxytoluene, and edetate calcium disodium in a ratio to provide a composition containing 0.05% to 5% active agent by weight.

Ointment Formulation for Topical Administration

A compound of the invention is combined with mineral oil, paraffin, propylene carbonate, white petrolatum and white wax to provide a composition containing 0.05% to 5% active agent by weight.

Cream Formulation for Topical Administration

Mineral oil is combined with a compound of the invention, propylene glycol, isopropyl palmitate, polysorbate 60, cetyl alcohol, sorbitan monostearate, polyoxyl 40 stearate, sorbic acid, methylparaben and propylparaben to form an oil phase, which is combined with purified water by shear blending to provide a composition containing 0.05% to 5% active agent by weight.

Cream Formulation for Topical Administration

A cream formulation comprising a compound of the invention, benzyl alcohol, cetyl alcohol, citric acid anhydrous, mono and di-glycerides, oleyl alcohol, propylene glycol, sodium cetostearyl sulphate, sodium hydroxide, stearyl alcohol, triglycerides, and water contains 0.05% to 5% active agent by weight.

Cream Formulation for Topical Administration

A cream formulation comprising a compound of the invention, cetostearyl alcohol, isopropyl myristate, propylene glycol, cetomacrogol 1000, dimethicone 360, citric acid, sodium citrate, and purified water, with imidurea, methylparaben, and propylparaben, as preservatives, contains 0.05% to 5% active agent by weight.

Utility

The compounds of the invention have been shown to be potent inhibitors of the JAK family of enzymes: JAK1, JAK2, JAK3, and TYK2. Inhibition of the family of JAK enzymes could inhibit signaling of many key pro-inflammatory cytokines. Thus the JAK inhibitors of the invention are expected to be useful in the treatment of inflammatory diseases such as ulcerative colitis, and other gastrointestinal inflammatory diseases such as Crohn's disease and immune checkpoint inhibitor induced colitis. The present JAK inhibitors are also expected to be useful in the treatment of atopic dermatitis and other inflammatory and pruritic skin diseases and in the treatment of respiratory conditions such as allergic rhinitis, asthma, and chronic obstructive pulmonary disease (COPD).

Gastrointestinal Inflammatory Disease

In addition to providing potent inhibition of JAK enzymes, compounds of the invention have been designed to be poorly absorbed to minimize systemic exposure. Selected compounds tested in cannulated rats showed low oral bioavailability. In addition, the compounds are designed to have their effect at the site of action, for example, in the colon. As described in Assays 6 and 7 below, the compound of Example 2 exhibited oral bioavailability in rat less than about 5% and a ratio of exposure in the colon to exposure in plasma upon oral administration greater than about 250.

Oxazolone-induced colitis is an experimental model that has a histological resemblance to human ulcerative colitis. As described below, the compound of Example 2, among other compounds of the invention, demonstrated activity in the oxazolone-induced colitis model in mice. Further, when tested in an immunosuppression model in mice, which probes systemic functional activity, the compound demonstrated minimal effect of immunosuppression at the same dose required to demonstrate efficacy in the oxazolone model. Thus the compound demonstrated anti-colitic activity without exhibiting systemic effects in preclinical models.

It is expected that a high colon to plasma ratio will provide robust, luminally-driven anti-inflammatory activity without associated, systemically-driven, adverse effects.

Such compounds are expected to be useful for a variety of gastrointestinal inflammatory indications that include, but are not limited to, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology,* 1996, 16, 144-150), Crohn's disease (Woywodt et al., *Eur J Gastroenterology Hepatology,* 1999, 11, 267-276), collagenous colitis (Kumawat et al., *Mol Immunology,* 2013, 55, 355-364), lymphocytic colitis (Kumawat et al., 2013), eosinophilic esophagitis (Weinbrand-Goichberg et al., *Immunol Res,* 2013, 56, 249-260), graft versus host disease-related colitis (Coghill et al., *Blood,* 2001, 117, 3268-3276), infectious colitis (Stallmach et al., *Int J Colorectal Dis,* 2004, 19, 308-315), Behcet's disease (Zhou et al., *Autoimmun Rev,* 2012, 11, 699-704), celiac disease (de Nitto et al., *World J Gastroenterol,* 2009, 15, 4609-4614), immune checkpoint inhibitor induced colitis (e.g., CTLA-4 inhibitor-induced colitis; (Yano et al., *J Translation Med,* 2014, 12, 191), PD-1- or PD-L1-inhibitor-induced colitis), and ileitis (Yamamoto et al., *Dig Liver Dis,* 2008, 40, 253-259) are characterized by elevation of certain pro-inflammatory cytokine levels. As many pro-inflammatory cytokines signal via JAK activation, compounds described in this application may be able to alleviate the inflammation and provide symptom relief.

In particular, the compounds of the invention are expected to be useful for the induction and maintenance of remission of ulcerative colitis, and for the treatment of Crohn's disease, immune checkpoint inhibitor induced colitis, and the gastrointestinal adverse effects in graft versus host disease.

In one aspect, therefore, the invention provides a method of treating a gastrointestinal inflammatory disease in a mammal (e.g., a human), the method comprising administering to the mammal a compound of the invention or a pharmaceutical composition comprising a pharmaceutically-acceptable carrier and a compound of the invention.

The invention further provides a method of treating ulcerative colitis in a mammal, the method comprising administering to the mammal a compound of the invention or a pharmaceutical composition comprising a pharmaceutically-acceptable carrier and a compound of the invention.

When used to treat ulcerative colitis, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 1 to about 400 mg/day of active agent, including from about 5 to about 300 mg/day and from about 20 to about 70 mg per day of active agent for an average 70 kg human.

Combination Therapy

Compounds of the invention may also be used in combination with one or more agents which act by the same mechanism or by different mechanisms to effect treatment of gastrointestinal inflammatory disorders. Useful classes of agents for combination therapy include, but are not limited to, aminosalicylates, steroids, systemic immunosuppressants, anti-TNFα antibodies, anti-VLA-4 antibodies, anti-integrin α$_4$β$_7$ antibodies, anti-bacterial agents, and anti-diarrheal medicines.

Aminosalicylates that may be used in combination with the present JAK inhibitor compounds include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin α$_4$β$_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, Gut, 2012, 61, 918-932; Lam et al., *Immunotherapy*, 2014, 6, 963-971.)

In another aspect, therefore, the invention provides a therapeutic combination for use in the treatment of gastrointestinal inflammatory disorders, the combination comprising a compound of the invention and one or more other therapeutic agents useful for treating gastrointestinal inflammatory disorders. For example, the invention provides a combination comprising a compound of the invention and one or more agents selected from aminosalicylates, steroids, systemic immunosuppressants, anti-TNFα antibodies, anti-VLA-4 antibodies, anti-integrin α$_4$β$_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the invention.

Also provided, therefore, is a pharmaceutical composition comprising a compound of the invention and one or more other therapeutic agents useful for treating gastrointestinal inflammatory disorders.

Further, in a method aspect, the invention provides a method of treating gastrointestinal inflammatory disorders, the method comprising administering to the mammal a compound of the invention and one or more other therapeutic agents useful for treating gastrointestinal inflammatory disorders.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Inflammatory Skin Disease

Atopic dermatitis, for example, has been associated with elevation of proinflammatory cytokines that rely on the JAK-STAT pathway, in particular, IL-4, IL-5, IL-10, IL-13, and IFNγ. Since compounds of the invention exhibit potent inhibition at all four JAK enzymes, they are expected to potently inhibit the proinflammatory cytokines characteristic of atopic dermatitis and other inflammatory skin diseases. In particular, the compound 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile, disclosed in Example 2, exhibited IC$_{50}$ values of 50 nM or less for inhibition of IL-4, IL-13, and IFNγ in the cellular assays described in Assays 4, 2, and 5, respectively. The compound also exhibited a dose- and concentration-dependent effect in a TPA-induced irritant contact dermatitis model in mice. Furthermore, model cream and ointment formulations of the compound of Example 2 have demonstrated sustained dermal levels for at least 2 days in mice and at least 7 days in mini-pig without detectable plasma exposure.

It is expected that sustained dermal levels of JAK inhibitors in the absence of significant systemic levels will result in potent local anti-inflammatory and anti-pruritic activity in the skin without systemically-driven adverse effects. Such compounds are expected to be beneficial in a number of dermal inflammatory or pruritic conditions that include, but are not limited to atopic dermatitis, alopecia areata, vitiligo, cutaneous T cell lymphoma, prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT,* 2013, 2, e24137), alopecia areata (Xing et al., *Nat Med.* 2014, 20, 1043-1049), vitiligo (Craiglow et al, *JAMA Dermatol.* 2015, 151, 1110-1112), cutaneous T cell lymphoma (Netchiporouk et al., *Cell Cycle.* 2014; 13, 3331-3335), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compounds of the invention may be able to alleviate associated dermal inflammation or pruritus driven by these cytokines. In particular, compounds of the invention are expected to be useful for the treatment of atopic dermatitis and other inflammatory skin diseases.

In one aspect, therefore, the invention provides a method of treating an inflammatory skin disease in a mammal (e.g., a human), the method comprising applying a pharmaceutical composition comprising a compound of the invention and a pharmaceutical carrier to the skin of the mammal. In one aspect, the inflammatory skin disease is atopic dermatitis.

Compounds of the invention may also be used in combination with gram positive antibiotics, such as mupirocin and fusidic acid, to treat inflammatory skin disease. In one aspect, therefore, the invention provides a method of treating an inflammatory skin disease in a mammal, the method comprising applying a compound of the invention and a gram positive antibiotic to the skin of the mammal. In another aspect, the invention provides a pharmaceutical composition comprising a compound of the invention, a gram positive antibiotic, and a pharmaceutically-acceptable carrier.

Compounds of the invention have been demonstrated to be potent inhibitors of the JAK1, JAK2, JAK3, and TYK2 enzymes in enzyme binding assays and to have potent functional activity without cytotoxicity in cellular assays, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
CPME=cyclopentyl methyl ether
d=day(s)
DIPEA=N,N-diisopropylethylamine
DMF=N,N-dimethylformamide
DMSO=dimethyl sulfoxide
EtOAc=ethyl acetate
EtOH=ethyl alcohol
h=hour(s)
HATU=N,N,N',N'-tetramethyl-O-(7-azabenzotriazol-1-yl)uronium hexafluorophosphate
IPA=isopropyl alcohol
MeOH=methanol
min=minute(s)
NMP=N-methylpyrrolidone
RT=room temperature
TEA=triethylamine
THF=tetrahydrofuran
TFA=trifluoroacetic acid
Xantphos=4,5-bis(diphenylphosphino)-9,9-dimethylxanthene
Xphos=dicyclohexylphosphino-2',4',6'-triisopropylbiphenyl
XphosPd G2=chloro(2-dicyclohexylphosphino-2',4',6'-triisopropyl-1,1'-biphenyl)[2-(2'-amino-1,1'-biphenyl)]palladium(II)

Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as $CD_3OD$, $CDCl_3$, or $d_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Unless otherwise indicated the following conditions were used for preparative HPLC purifications.
Column: C18, 5 μm 21.2×150 mm or C18, 5 μm 21×250 mm or C14, 5 μm 21×150 mm
Column temperature: Room Temperature
Flow rate: 20.0 mL/min
Mobile Phases: A=Water+0.05% TFA
 B=ACN+0.05% TFA,
Injection volume: (100-15004)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 μL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytic HPLC Conditions
Method A
Column: LUNA C18 (2), 150×4.60 mm, 3 μm
Column temperature: 37° C.
Flow rate: 1.0 mL/min
Injection volume: 5 μL
Sample preparation: Dissolve in 1:1 ACN:water
Mobile Phases: A=Water:ACN:TFA (98:2:0.05)
 B=Water:ACN:TFA (2:98:0.05)
Detector wavelength: 250 nm
Gradient: 32 min total (time (min)/% B): 0/2, 10/20, 24/90, 29/90, 30/2, 32/2
Method B
Column: LUNA C18 (2), 150×4.60 mm, 3 μm
Column temperature: 37° C.
Flow rate: 1.0 mL/min
Injection volume: 10 μL
Sample preparation: Dissolve in 1:1 ACN:water
Mobile Phases: A=Water:ACN:TFA (98:2:0.05)
 B=Water:ACN:TFA (10:90:0.05)
Detector wavelength: 254 nm
Gradient: 35 min total (time (min)/% B): 0/2, 20/25, 23/90, 26/90, 27/2, 35/2

Preparation 1: (3-((2,6-Dichloropyrimidin-4-yl)amino)-1H-pyrazol-5-yl)methanol

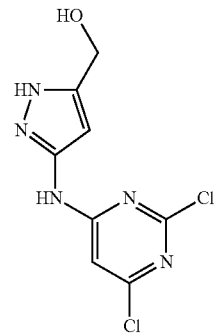 [SMILES: OCc1cc(Nc2cc(Cl)nc(Cl)n2)n[nH]1]

To a mixture of 2,4,6-trichloropyrimidine (8.0 g, 43.7 mmol) and (3-amino-1H-pyrazol-5-yl)methanol (7.4 g, 65.4 mmol) in EtOH (80 mL) was added DIPEA (11.3 g, 87.2 mmol). The reaction mixture was stirred at 20° C. for 12 h and filtered to give the title intermediate (6.5 g, 57% yield) as a white solid. (m/z): [M+H]$^+$ calcd for $C_8H_7Cl_2N_5O$ 260.00 found 260.0.

Preparation 2: (3-((2-(((1R,3s,5S)-8-azabicyclo[3.2.1]octan-3-yl)amino)-6-methoxypyrimidin-4-yl)amino)-1H-pyrazol-5-yl)methanol

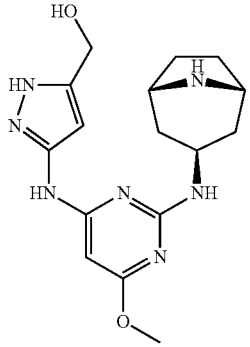 [SMILES: COc1cc(Nc2cc(CO)[nH]n2)nc(N[C@@H]2C[C@H]3CC[C@@H](C2)N3)n1]

(a) tert-Butyl (1R,3s,5S)-3-((4-chloro-6-((5-(hydroxymethyl)-/H-pyrazol-3-yl)amino)pyrimidin-2-yl)amino)-8-azabicyclo[3.2.1]octane-8-carboxylate A mixture of (3-((2,6-dichloropyrimidin-4-yl)amino)-1H-pyrazol-5-yl)methanol (6.0 g, 23.1 mmol), tert-butyl (1R,3s,5S)-3-amino-8-azabicyclo[3.2.1]octane-8-carboxylate (6.3 g, 27.7 mmol), and DIPEA (6.0 g, 46.2 mmol) in DMSO (60 mL) was stirred at 100° C. for 12 h. The reaction mixture was combined with the product of a pilot scale run and poured into water (800 mL). The precipitate was filtered and dried in vacuo. The residue was re-crystallized from EtOAc (500 mL) and petroleum ether (500 mL) to afford the title intermediate (5.6 g, 50% yield) as a gray solid. Structure confirmed by NMR.

(b) tert-Butyl (1R,3s,5S)-3-((4-((5-(hydroxymethyl)-1H-pyrazol-3-yl)amino)-6-methoxypyrimidin-2-yl)amino)-8-azabicyclo[3.2.1]octane-8-carboxylate To a solution of sodium methoxide (2.4 g, 44.5 mmol) in MeOH (30 mL) was added the product of the previous step (2.0 g, 4.45 mmol) at 20° C. The reaction mixture was stirred in a sealed tube at 100° C. for 8 h. The reaction mixture was combined with the product of a pilot scale run, poured into water (30 mL), and extracted with EtOAc (3×50 mL). The organic layer was washed with brine (2×30 mL), dried over $Na_2SO_4$, filtered, and concentrated in vacuo. The residue was purified by preparative HPLC (Daiso 250×50 mm 10 μm, 80 mL/min, 30-55% ACN+0.1% TFA/ACN) to afford the title intermediate (0.7 g, 32% yield) as a white solid. (m/z): $[M+H]^+$ calcd for $C_{21}H_{31}N_7O_4$ 446.24 found 446.2.

(c) (3-((2-(((1R,3s,5S)-8-azabicyclo[3.2.1]octan-3-yl)amino)-6-methoxypyrimidin-4-yl)amino)-1H-pyrazol-5-yl)methanol A solution of the product of the previous step (0.7 g, 1.57 mmol) in 4 M HCl in EtOAc (20 mL) was stirred at 20° C. for 2 h, and concentrated in vacuo to provide the HCl salt of the title compound (0.6 g, 99% yield) as a white solid. (m/z): $[M+H]^+$ calcd for $C_{16}H_{23}N_7O_2$ 346.19 found 346.2.

Preparation 3: tert-Butyl (1R,3s,5S)-3-(methylamino)-8-azabicyclo[3.2.1]octane-8-carboxylate

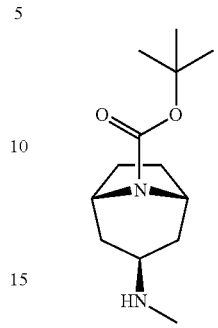

(a) tert-butyl (1R,3s,5S)-3-(((benzyloxy)carbonyl)amino)-8-azabicyclo[3.2.1]octane-8-carboxylate A solution of tert-butyl (1R,3s,5S)-3-amino-8-azabicyclo[3.2.1]octane-8-carboxylate (5.21 g, 23.00 mmol), DMF (115 ml), and triethylamine (6.41 mL, 46.0 mmol) was stirred at RT for 15 min. Benzyl chloroformate (3.56 mL, 25.3 mmol) was added dropwise and the reaction mixture was stirred at RT for 3 h, quenched with water, and extracted with EtOAc (4×20 mL). The combined organic fractions were washed with brine (2×20 mL), dried over sodium sulfate, filtered, and concentrated to afford a yellow oil which was purified by column chromatography (120 g column; 0-70% EtOAc in hexanes) to afford the title intermediate as a thick, clear oil (3.79 g, 36% yield; 79% purity). (m/z): $[M+H]^+$ calcd for $C_{20}H_{28}N_2O_4$ 361.20 found 361.2.

(b) tert-butyl(1R,3s,5S)-3-(((benzyloxy)carbonyl)(methyl)amino)-8-azabicyclo[3.2.1]octane-8-carboxylate A solution of the product of the previous step (2.99 g, 8.29 mmol) in DMF (41.5 mL) was cooled to 0° C. and sodium hydride, 60% dispersion in mineral oil (0.398 g, 16.58 mmol) was added in one portion. The resulting suspension was stirred at 0° C. for 15 min, and then iodomethane (1.03 mL, 16.58 mmol) was added dropwise and the resulting cloudy, pale yellow mixture was stirred at 0° C. for 15 min, warmed to RT and stirred for 2 h. The reaction mixture was quenched with water and extracted with EtOAc (4×20 mL). The combined organic fractions were washed with brine (2×20 mL), dried over sodium sulfate, filtered, and concentrated to afford a clear, pale yellow oil, which was purified by column chromatography (80 g column; 0-70% EtOAc in hexanes) to afford the title intermediate as a clear, colorless thick oil (2.07 g, 65% yield; 97% purity). (m/z): $[M+H]^+$ calcd for $C_{21}H_{30}N_2O_4$ 375.22 found 375.5.

(c) tert-Butyl (1R,3s,5S)-3-(methylamino)-8-azabicyclo[3.2.1]octane-8-carboxylate To a 100 mL flask was added palladium, 10% wt. on carbon (0.577 g, 0.542 mmol). The material was exposed to nitrogen and then a solution of the product of the previous step (1.015 g, 2.71 mmol) in MeOH (54.2 mL) was slowly added by pipette. A hydrogen gas balloon was attached. The flask was evacuated and back-filled with hydrogen three times before opening the atmosphere fully to $H_2$ gas. The reaction mixture was stirred at RT for 16 h, filtered through a pad of Celite®, and concentrated to afford a clear oil, which was purified by column chromatography 40 g column; 0-100% MeOH in DCM) to afford the product as a clear oil. The column was flushed with 10:1 MeOH:TEA. The filtrate was concentrated to provide a thick, clear oil with white solid which was dissolved in EtOAc, filtered, combined with the clear oil product and concentrated to provide the title intermediate (0.559 g, 86% yield) (m/z): [M+H]+ calcd for $C_{13}H_{24}N_2O_2$ 241.18 found 241.3.

Preparation 4: (3-((2-(((1R,3s,5S)-8-azabicyclo[3.2.1]octan-3-yl)(methyl)amino)-6-methoxypyrimidin-4-yl)amino)-1H-pyrazol-5-yl)methanol

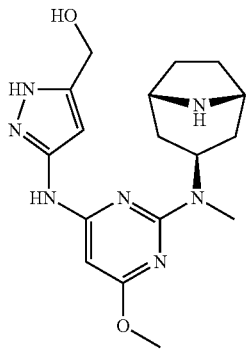 [SMILES: COc1cc(Nc2cc(CO)[nH]n2)nc(N(C)[C@@H]2C[C@H]3CC[C@@H](C2)N3)n1]

(a) tert-Butyl (1R,3s,5S)-3-((4-chloro-6-((5-(hydroxymethyl)-1H-pyrazol-3-yl)amino)pyrimidin-2-yl)(methyl)amino)-8-azabicyclo[3.2.1]octane-8-carboxylate A solution of (3-((2,6-dichloropyrimidin-4-yl)amino)-1H-pyrazol-5-yl)methanol (200 mg, 0.77 mmol), tert-butyl (1R,3s,5S)-3-(methylamino)-8-azabicyclo[3.2.1]octane-8-carboxylate (194 mg, 0.81 mmol) and TEA (0.29 mL, 1.92 mmol) were stirred in DMSO (5 mL) overnight at 60° C. The reaction mixture was concentrated in vacuo. The crude residue was purified by reverse phase chromatography to afford the title intermediate (143 mg, 0.31 mmol, 40% yield), which was used directly in the next step.

(b) (3-((2-(((1R,3s,5S)-8-Azabicyclo[3.2.1]octan-3-yl)(methyl)amino)-6-chloropyrimidin-4-yl)amino)-1H-pyrazol-5-yl)methanol To the product of the previous step (143 mg, 0.31 mmol) dissolved in ACN (3.0 mL) was added 4 N HCl in dioxane (1.156 mL 4.62 mmol) and the reaction mixture was stirred at RT for 30 min. The reaction mixture was concentrated in vacuo to provide the HCl salt of the title intermediate which was used without purification in the next step.

(c) (3-((2-(((1R,3s,5S)-8-azabicyclo[3.2.1]octan-3-yl)(methyl)amino)-6-methoxypyrimidin-4-yl)amino)-1H-pyrazol-5-yl)methanol To a stirred solution of the product of the previous step (112 mg, 0.280 mmol) in MeOH (5 mL) was added 50% sodium methoxide in MeOH (0.960 mL, 8.39 mmol). The reaction mixture was heated in a sealed vial at 80° C. overnight. The reaction mixture was concentrated in vacuo and the crude residue was purified via reverse phase chromatography to afford the title product (27 mg, 0.057 mmol, 20% yield).

Preparation 5: (3-((2-(((1R,3s,5S)-9-azabicyclo[3.3.1]nonan-3-yl)amino)-6-methoxypyrimidin-4-yl)amino)-1H-pyrazol-5-yl)methanol

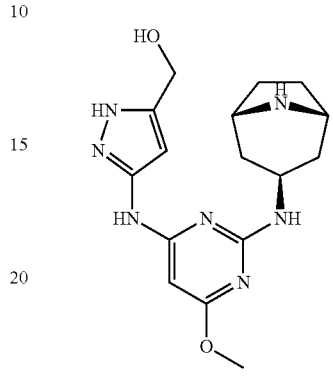

(a) tert-Butyl (1R,3s,5S)-3-((4-chloro-6-((5-(hydroxymethyl)-1H-pyrazol-3-yl)amino)pyrimidin-2-yl)amino)-9-azabicyclo[3.3.1]nonane-9-carboxylate To a mixture of (3-((2,6-dichloropyrimidin-4-yl)amino)-1H-pyrazol-5-yl)methanol (3.7 g, 14.2 mmol) and tert-butyl (1R,3s,5S)-3-amino-9-azabicyclo[3.3.1]nonane-9-carboxylate (4.1 g, 17.0 mmol) in DMSO (37 mL) was added DIPEA (3.7 g, 28.4 mmol) under nitrogen. The reaction was stirred at 120° C. for 12 h, poured into water (80 mL), extracted with EtOAc (3×100 mL), dried, and concentrated to provide crude product, which was washed with EtOAc (20 mL), to give the title intermediate (3.8 g, 56% yield) as a white solid.

(b) tert-Butyl (1R,3s,5S)-3-((4-((5-(hydroxymethyl)-1H-pyrazol-3-yl)amino)-6-methoxypyrimidin-2-yl)amino)-9-azabicyclo[3.3.1]nonane-9-carboxylate Four reactions were carried out in parallel. To a mixture of the product of the previous step (0.95 g, 2.0 mmol) in sodium methoxide in MeOH (10 mL) was stirred at 120° C. for 3 h in a sealed tube. The reaction mixture was added to water (50 mL) and extracted with EtOAc (3×50 mL). The organic layers were washed with brine (30 mL), dried over $Na_2SO_4$, and concentrated in vacuo. The residue was purified by preparative HPLC (Luna C18 250×50 mm 10 μm, ACN+0.1% TFA/ACN) to obtain the title intermediate (1.2 g combined product, 28% yield) as a brown solid. (m/z): [M+H]+ calcd for $C_{22}H_{33}N_7O_4$ 460.26 found 460.3.

(c) (3-((2-(((1R,3s,5S)-9-azabicyclo[3.3.1]nonan-3-yl)amino)-6-methoxypyrimidin-4-yl)amino)-1H-pyrazol-5-yl)methanol To the product of the previous step (1.2 g, 2.5 mmol) was added 4 M HCl in EtOAc (50 mL). The reaction was stirred at 25° C. for 2 h. The residue was combined with the product of a preparation at the 1.5 mmol scale and concentrated to provide the title intermediate (2.0 g, 100% yield) as a light yellow solid. (m/z): [M+H]+ calcd for $C_{17}H_{25}N_7O_2$ 360.43 found 360.4.

Preparation 6: (3-((2-(((1R,3s,5S)-9-Azabicyclo[3.3.1]nonan-3-yl)(methyl)amino)-6-methoxypyrimidin-4-yl)amino)-1H-pyrazol-5-yl)methanol

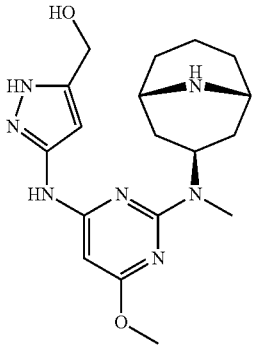

(a) tert-Butyl (1R,3s,5S)-3-((4-chloro-6-((5-(hydroxymethyl)-1H-pyrazol-3-yl)amino)pyrimidin-2-yl)(methyl)amino)-9-azabicyclo[3.3.1]nonane-9-carboxylate To a mixture of (3-((2,6-dichloropyrimidin-4-yl)amino)-1H-pyrazol-5-yl)methanol (6.5 g, 24.9 mmol), tert-butyl (1R,3s,5S)-3-(methylamino)-9-azabicyclo[3.3.1]nonane-9-carboxylate (6.9 g, 27.4 mmol) in DMSO (80 mL) was added DIPEA (6.4 g, 49.8 mmol) under nitrogen. The reaction mixture was stirred at 120° C. for 8 h, poured into water (80 mL), extracted with EtOAc (500 mL), dried, and concentrated to provide the crude product. The crude product was combined with the product of a separate preparation at the same scale and purified by preparative HPLC (Daiso 150×25 mm 5 μm, 80 mL/min, 35-60% ACN+0.1% TFA/ACN) to provide the title intermediate (16.0 g, 64% yield) as a light yellow solid. (m/z): [M+H]$^+$ calcd for $C_{22}H_{32}ClN_7O_3$ 478.23 found 478.2.

(b) tert-Butyl (1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonane-9-carboxylate To a mixture of the product of the previous step (2.0 g, 4.19 mmol) in MeOH (20 mL) was added sodium methoxide (2.2 g, 41.9 mmol). The reaction mixture was stirred at 120° C. for 6 h in a sealed tube for 12 h, poured into water (100 mL), diluted with EtOAc (800 mL), washed with brine (50 mL), dried, and concentrated to provide crude product. The crude product was combined with the product of a separate preparation at the 2 mmol scale and purified by preparative HPLC (Synergi Max-RP, 250×50 mm 10 μm, 80 mL/min, 25-50% ACN+0.1% TFA/ACN) to provide the title intermediate (2.1 g, 71% yield) as a white solid.

(c) (3-((2-(((1R,3s,5S)-9-Azabicyclo[3.3.1]nonan-3-yl)(methyl)amino)-6-methoxypyrimidin-4-yl)amino)-1H-pyrazol-5-yl)methanol To a mixture of the product of the previous step (2.1 g, 4.43 mmol) in EtOAc (20 mL) was added 4 M HCl in EtOAc (20 mL), and the reaction was stirred at 20° C. for 3 h and concentrated to provide the HCl salt of the product (2.0 g, 100% yield) as a white solid. (m/z): [M+H]$^+$ calcd for $C_{18}H_{27}N_7O_2$ 374.22 found 374.1.

Example 1: 1-(((1R,3s,5S)-3-((4-((5-(Hydroxymethyl)-1H-pyrazol-3-yl)amino)-6-methoxypyrimidin-2-yl)(methyl)amino)-8-azabicyclo[3.2.1]octan-8-yl)sulfonyl)azetidine-3-carbonitrile

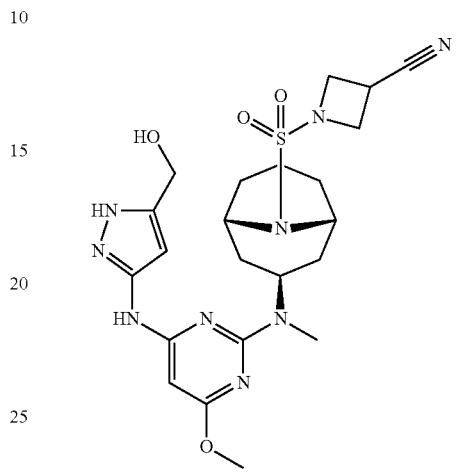

To a solution of (3-((2-(((1R,3s,5S)-8-azabicyclo[3.2.1]octan-3-yl(methyl)amino)-6-methoxypyrimidin-4-yl)amino)-1H-pyrazol-5-yl)methanol (15 mg, 0.042 mmol) in DMF (4.0 mL) was added DIPEA (0.022 ml, 0.125 mmol) followed by 3-cyano-1-azetidinesulfonylchloride (7.54 mg, 0.042 mmol). The reaction mixture was stirred at RT overnight. The solvent was removed in vacuo and the crude residue was purified by reverse-phase HPLC to provide the TFA salt of the title compound (3.2 mg). (m/z): [M+H]$^+$ calcd for $C_{21}H_{29}N_9O_4S$ 504.21 found 504.1.

Example 2: 1-(((1R,3s,5S)-3-((4-((5-(Hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile

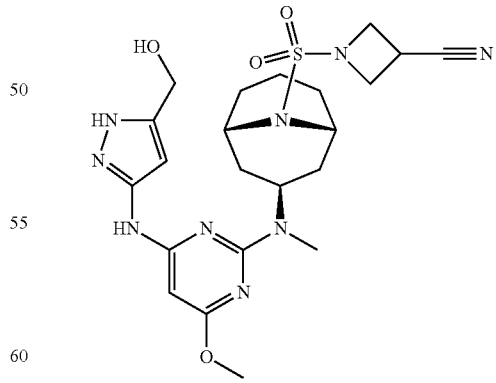

To a solution of (3-((2-(((1R,3s,5S)-9-azabicyclo[3.3.1]nonan-3-yl)(methyl)amino)-6-methoxypyrimidin-4-yl)amino)-1H-pyrazol-5-yl)methanol HCl (150 mg, 0.402 mmol) and DIPEA (0.351 mL, 2.008 mmol) in DMF (3 mL) at 0° C. was added 3-cyano-1-azetidinesulfonylchloride (72.5 mg, 0.402 mmol) and the reaction mixture was stirred at 0° C. for 10 min and then at RT for 15 h. The reaction mixture was concentrated in vacuo to yield a red liquid which was purified by preparative HPLC to yield the TFA salt of the title compound (72.4 mg, 0.115 mmol, 28.5% yield) as a white solid. (m/z): [M+H]+ calcd for $C_{22}H_{31}H_9O_4S$ 518.22 found 518.

Example 3: (3-((6-methoxy-2-(methyl((1R,3s,5S)-9-(methylsulfonyl)-9-azabicyclo[3.3.1]nonan-3-yl)amino)pyrimidin-4-yl)amino)-1H-pyrazol-5-yl)methanol

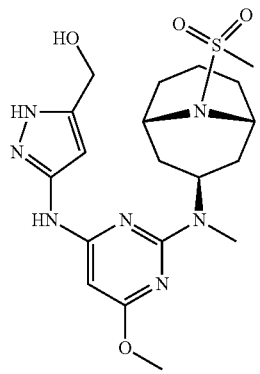 [SMILES: COc1cc(Nc2cc(CO)[nH]n2)nc(N(C)[C@@H]2C[C@H]3CCC[C@@H](C2)N3S(C)(=O)=O)n1]

A solution of (3-((2-(((1R,3s,5S)-9-azabicyclo[3.3.1]nonan-3-yl)(methyl)amino)-6-methoxypyrimidin-4-yl)amino)-1H-pyrazol-5-yl)methanol HCl (250 mg, 0.669 mmol) in DMF (7.0 mL) was cooled to 0° C. and DIPEA (0.35 mL, 2.008 mmol) was added in one portion followed by methanesulfonyl chloride (0.053 mL, 77 mg, 0.676 mmol) added dropwise. The reaction mixture was stirred overnight, dissolved in 1:1 acetic acid:water (6 mL), filtered, and purified by preparative HPLC to provide the TFA salt of the title compound (94 mg, 31% yield) as a white powder. (m/z): [M+H]+ calcd for $C_{19}H_{29}N_7O_4S$ 452.15 found 452.2.

Example 4: (3-((6-methoxy-2-(((1R,3s,5S)-9-((2-methoxyethyl)sulfonyl)-9-azabicyclo[3.3.1]nonan-3-yl)(methyl)amino)pyrimidin-4-yl)amino)-1H-pyrazol-5-yl)methanol

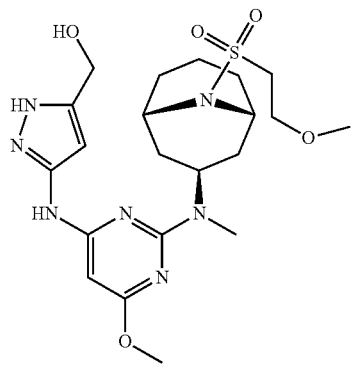 [SMILES: COCCS(=O)(=O)N1[C@@H]2CCC[C@H]1C[C@H](N(C)c1nc(Nc3cc(CO)[nH]n3)cc(OC)n1)C2]

A solution of (3-((2-(((1R,3s,5S)-9-azabicyclo[3.3.1]nonan-3-yl)(methyl)amino)-6-methoxypyrimidin-4-yl)amino)-1H-pyrazol-5-yl)methanol HCl (250 mg, 0.703 mmol) in DMF (7.0 mL) was cooled to 0° C. and DIPEA (0.35 mL, 2.008 mmol) was added in one portion followed by 2-methoxy-ethanesulfonyl chloride (111 mg, 0.676 mmol) added dropwise. The reaction mixture was stirred overnight, dissolved in 1:1 acetic acid:water (6 mL), filtered, and purified by preparative HPLC to provide the TFA salt of the title compound (41 mg, 12% yield) as a white solid. (m/z): [M+H]+ calcd for $C_{11}H_{33}N_7O_5S$ 496.23 found 496.2.

Example 5: 3-((1R,3s,5S)-3-((4-((5-(hydroxymethyl)-1H-pyrazol-3-yl)amino)-6-methoxypyrimidin-2-yl)(methyl)amino)-8-azabicyclo[3.2.1]octan-8-yl)-propanenitrile

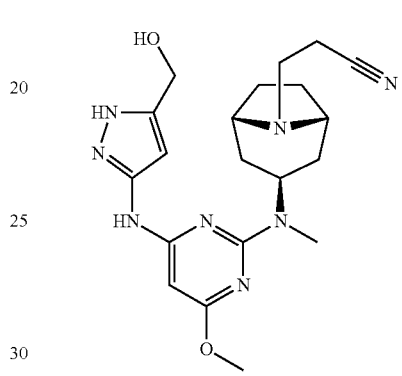

To a solution of (3-((2-(((1R,3s,5S)-8-azabicyclo[3.2.1]octan-3-yl(methyl)amino)-6-methoxypyrimidin-4-yl)amino)-1H-pyrazol-5-yl)methanol (15 mg, 0.042 mmol) in MeOH (4.0 mL) was added DIPEA (0.022 mL, 0.125 mmol) followed by acrylonitrile (2.70 µL, 0.042 mmol). The reaction mixture was stirred at RT overnight, concentrated in vacuo and purified by reverse-phase HPLC to provide the TFA salt of the title compound (4.3 mg). (m/z): [M+H]+ calcd for $C_{20}H_{28}N_8O_2$ 413.23 found 413.2.

Example 6: 5-(((1R,3s,5S)-3-((4-((5-(hydroxymethyl)-1H-pyrazol-3-yl)amino)-6-methoxypyrimidin-2-yl)amino)-9-azabicyclo[3.3.1]nonan-9-yl)methyl)picolinonitrile

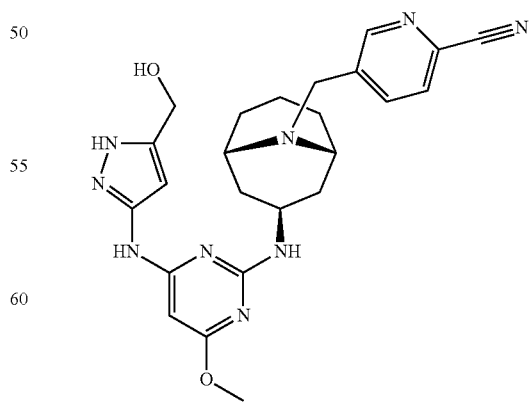

Diisopropylamine (0.032 mL, 0.225 mmol) (0.256 mL) was added to a 0.15 M solution of (3-((2-(((1R,3s,5S)-9- azabicyclo[3.3.1]nonan-3-yl)amino)-6-methoxypyrimidin-4-yl)amino)-1H-pyrazol-5-yl)methanol (29.8 mg, 0.075 mmol) in DMF and the solution was swirled to dissolve all the material. To the solution was added a 0.23 M solution of 4-(chloromethyl)-picolinonitrile) (0.5 mL, 34 mg, 0.113 mmol) in DMF and the reaction mixture was stirred at RT overnight. Polystyrene-thiophenol resin (0.115 g, 0.150 mmol) was added, the reaction mixture was stirred at RT for 4 h and filtered. The reaction vessel was washed with DMF (0.5 mL) and the washes were combined, concentrated by rotary evaporation, dissolved in 1:1 acetic acid:water, filtered, and purified by reverse-phase HPLC to provide the TFA salt of the title compound (6.4 mg). (m/z): [M+H]$^+$ calcd for $C_{24}H_{29}N_9O_2$ 476.24 found 476.1.

Example 7: 5-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)methyl)nicotinonitrile

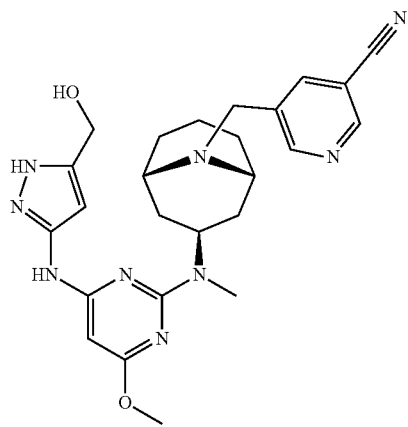 [SMILES: COc1cc(Nc2cc(CO)[nH]n2)nc(N(C)[C@@H]2C[C@H]3CCC[C@@H](C2)N3Cc2cncc(C#N)c2)n1]

A solution of (3-((2-(((1R,3s,5S)-9-azabicyclo[3.3.1]nonan-3-yl)(methyl)amino)-6-methoxypyrimidin-4-yl)amino)-1H-pyrazol-5-yl)methanol HCl (20 mg, 0.054 mmol), 5-(bromomethyl)nicotinonitrile (10.55 mg, 0.054 mmol) and potassium carbonate (22.20 mg, 0.161 mmol) were stirred in DMF (6.0 mL) at 60° C. overnight. The reaction mixture was concentrated in vacuo and purified by reverse-phase HPLC to provide the TFA salt of the title intermediate (3.7 mg). (m/z): [M+H]$^+$ calcd for $C_{25}H_{31}N_9O_2$ 490.26 found 490.2.

Example 8: Isobutyl (1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonane-9-carboxylate

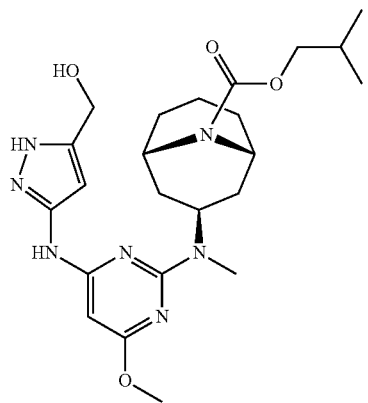 [SMILES: COc1cc(Nc2cc(CO)[nH]n2)nc(N(C)[C@@H]2C[C@H]3CCC[C@@H](C2)N3C(=O)OCC(C)C)n1]

To a solution of (3-((2-(((1R,3s,5S)-9-azabicyclo[3.3.1]nonan-3-yl(methyl)amino)-6-methoxypyrimidin-4-yl)amino)-1H-pyrazol-5-yl)methanol, HCl (25 mg, 0.061 mmol) and DIPEA (42.6 µL, 0.244 mmol) in DMF (305 µL) at 0° C. was added isobutyl chloroformate (10 mg, 0.073 mmol) in DMF (305 µL) dropwise. The reaction mixture was stirred at 0° C. for 5 min and then allowed to reach RT. After 24 h, the reaction mixture was concentrated, dissolved in 1:1 ACN:water and purified by reverse-phase HPLC to provide the TFA salt of the title compound (6.4 mg). (m/z): [M+H]$^+$ calcd for $C_{23}H_{35}N_7O_4$ 474.28 found 474.2.

Example 9: 2,2-difluoro-1-((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)ethan-1-one

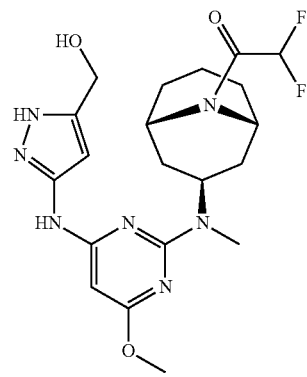 [SMILES: COc1cc(Nc2cc(CO)[nH]n2)nc(N(C)[C@@H]2C[C@H]3CCC[C@@H](C2)N3C(=O)C(F)F)n1]

HATU (0.029 g, 0.077 mmol) was added to a solution of 2,2-difluoroacetic acid (6.72 mg, 0.070 mmol) in DMF (3 mL) and the reaction mixture was stirred at RT for 5 min to prepare a 0.14 M solution of the activated acid. The 0.14 M solution of the activated acid (0.5 mL, 0.070 mmol) was added to a solution of (3-((2-(((1R,3s,5S)-9-azabicyclo[3.3.1]nonan-3-yl)(methyl)amino)-6-methoxypyrimidin-4-yl)amino)-1H-pyrazol-5-yl)methanol HCl (29 mg, 0.070 mmol) and DIPEA (0.049 mL, 0.280 mmol) in DMF and the reaction mixture was stirred at RT for 30 min, concentrated in vacuo and the resulting residue was dissolved in 1:1 acetic acid:water and purified by reverse-phase HPLC to provide the TFA salt of the title compound (3.9 mg). (m/z): [M+H]$^+$ calcd for $C_{20}H_{27}N_7O_3$ 452.21 found 452.1.

Using similar synthetic methods, the compounds of Tables 1-3 were prepared.

TABLE 1

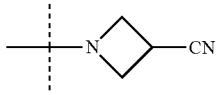

| Ex No. | n | R² | R⁴ | Formula | Calc [M + H]⁺ | Found [M + H]⁺ |
|---|---|---|---|---|---|---|
| 1-1 | 1 | H | azetidin-1-yl | $C_{19}H_{28}N_8O_4S$ | 465.20 | 465 |
| 1-2 | 1 | H | ![azetidine-CN] | $C_{20}H_{27}N_9O_4S$ | 490.19 | 490 |
| 1-3 | 1 | H | pyridin-3-yl | $C_{21}H_{26}N_8O_4S$ | 487.18 | 487.2 |
| 1-4 | 1 | H | phenyl | $C_{22}H_{27}N_7O_4S$ | 486.18 | 486.3 |
| 1-5 | 2 | H | azetidin-1-yl | $C_{20}H_{30}N_8O_4S$ | 479.21 | 479.1 |
| 1-6 | 2 | H | ![azetidine-CN] | $C_{21}H_{29}N_9O_4S$ | 504.21 | 504.1 |
| 1-7 | 2 | H | 5-fluoropyridin-3-yl | $C_{22}H_{27}FN_8O_4S$ | 519.19 | 519.1 |
| 1-8 | 2 | H | phenyl | $C_{23}H_{29}N_7O_4S$ | 500.20 | 500.1 |
| 1-9 | 2 | H | —$C_2H_5$ | $C_{19}H_{29}N_7O_4S$ | 452.20 | 452.1 |
| 1-10 | 2 | H | —$CH_2$-cyclopropyl | $C_{21}H_{31}N_7O_4S$ | 478.22 | 478.1 |
| 1-11 | 2 | H | pyridin-3-yl | $C_{22}H_{28}N_8O_4S$ | 501.20 | 501.1 |
| 1-12 | 2 | —$CH_3$ | —$(CH_2)_2CN$ | $C_{21}H_{30}N_8O_4S$ | 491.21 | 491 |
| 1-13 | 2 | —$CH_3$ | pyrrolidin-1-yl | $C_{22}H_{34}N_8O_4S$ | 507.24 | 507.2 |
| 1-14 | 2 | —$CH_3$ | cyclopropyl | $C_{21}H_{31}N_7O_4S$ | 478.22 | 478.1 |
| 1-15 | 2 | —$CH_3$ | pyridin-3-yl | $C_{23}H_{30}N_8O_4S$ | 515.21 | 515.1 |
| 1-16 | 2 | —$CH_3$ | phenyl | $C_{24}H_{31}N_7O_4S$ | 514.22 | 514.1 |
| 1-17 | 2 | —$CH_3$ | azetidin-1-yl | $C_{21}H_{32}N_8O_4S$ | 493.23 | 493.2 |
| 1-18 | 2 | —$CH_3$ | —$CH_2$-cyclopropyl | $C_{22}H_{33}N_7O_4S$ | 492.23 | 492.2 |
| 1-19 | 2 | —$CH_3$ | 5-fluoropyridin-3-yl | $C_{23}H_{29}FN_8O_4S$ | 533.20 | 533.1 |

TABLE 2

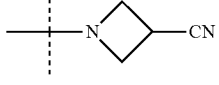

| Ex No. | n | R² | R¹ | Formula | Calc [M + H]⁺ | Found [M + H]⁺ |
|---|---|---|---|---|---|---|
| 2-1 | 1 | H | —$CH_2$-pyridin-4-yl | $C_{22}H_{28}N_8O_2$ | 437.23 | 437 |
| 2-2 | 2 | H | —$CH_2$-pyridin-4-yl | $C_{23}H_{30}N_8O_2$ | 451.25 | 451.2 |

TABLE 2-continued

[Structure with pyrazole, pyrimidine, and bicyclic amine with R1, R2, n substituents]

| Ex No. | n | R² | R¹ | Formula | Calc [M + H]⁺ | Found [M + H]⁺ |
|---|---|---|---|---|---|---|
| 2-3 | 2 | H | (4-methyl-2-cyanopyridin-4-yl)methyl | $C_{24}H_{29}N_9O_2$ | 476.24 | 476.2 |
| 2-4 | 2 | H | —CH₂-pyridin-3-yl | $C_{23}H_{30}N_8O_2$ | 451.25 | 451.2 |
| 2-5 | 2 | —CH₃ | —(CH₂)₂CN | $C_{21}H_{30}N_8O_2$ | 427.25 | 427 |
| 2-6 | 2 | —CH₃ | (1-cyanocyclopropyl)methyl | $C_{23}H_{32}N_8O_2$ | 453.27 | 453 |
| 2-7 | 2 | —CH₃ | —CH₂-pyridin-4-yl | $C_{24}H_{32}N_8O_2$ | 465.27 | 465.1 |
| 2-8 | 2 | —CH₃ | (2-cyanopyridin-4-yl)methyl | $C_{25}H_{31}N_9O_2$ | 490.26 | 490.2 |

TABLE 3

[Structure with pyrazole, pyrimidine, and bicyclic amine with R², R⁵, n substituents and carbonyl]

| Ex No. | n | R² | R⁵ | Formula | Calc [M + H]⁺ | Found [M + H]⁺ |
|---|---|---|---|---|---|---|
| 3-1 | 2 | H | —CHF₂ | $C_{19}H_{25}F_2N_7O_3$ | 438.20 | 438.1 |
| 3-2 | 2 | —CH₃ | —O-isobutyl | $C_{23}H_{35}N_7O_4$ | 474.28 | 474.2 |
| 3-3 | 2 | —CH₃ | —OCH₃ | $C_{20}H_{29}N_7O_4$ | 432.23 | 432.2 |
| 3-4 | 2 | —CH₃ | morpholin-1-yl | $C_{23}H_{34}N_8O_4$ | 487.27 | 487.2 |
| 3-5 | 2 | —CH₃ | —CH₂-cyclopropyl | $C_{23}H_{33}N_7O_3$ | 456.26 | 456.2 |
| 3-6 | 2 | —CH₃ | —CH₃ | $C_{20}H_{29}N_7O_3$ | 416.23 | 416.1 |
| 3-7 | 2 | —CH₃ | cyclopentyl | $C_{24}H_{35}N_7O_3$ | 470.28 | 470.2 |
| 3-8 | 2 | —CH₃ | cyclobutyl | $C_{23}H_{33}N_7O_3$ | 456.26 | 456.2 |

Example 10: 1-(((1R,3s,5S)-3-((4-((5-(Hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile

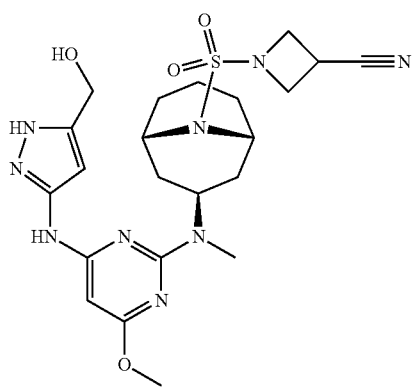 [SMILES: COc1cc(Nc2cc(CO)[nH]n2)nc(N(C)[C@@H]2C[C@H]3CCC[C@@H](C2)N3S(=O)(=O)N2CC(C#N)C2)n1]

(a) 5-((((triisopropylsilyl)oxy)methyl)-1H-pyrazol-3-amine (3')

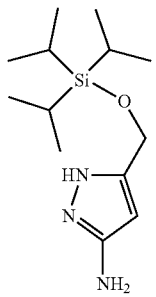

To a 100 mL flask was added (3-amino-1H-pyrazol-5-yl)methanol (5.8 g, 51.3 mmol), 1-methyl-2-pyrrolidinone (58.0 mL) and imidazole (4.54 g, 66.7 mmol) followed by triisopropylsilyl chloride (11.95 mL, 56.4 mmol). The reaction mixture was stirred at 22° C. overnight and then EtOAc (145 mL) and water (145 mL) were added. The layers were separated and the organic layer was washed with water (145 mL) and brine (15%, 100 mL), dried over $Na_2SO_4$, and evaporated under reduced pressure to provide the title intermediate (13.33 g, 49.5 mmol, 96% yield) HPLC Method A Retention time 19.00 min.

(b) tert-butyl (1R,3s,5S)-3-((4-chloro-6-methoxypyrimidin-2-yl)(methyl)amino)-9-azabicyclo[3.3.1]nonane-9-carboxylate (9')

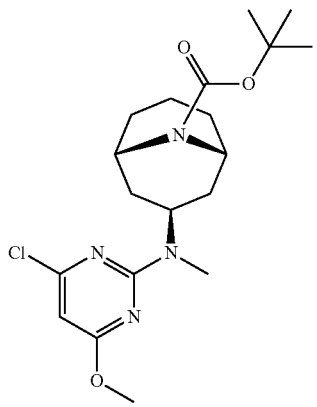

To a mixture of 2,4-dichloro-6-methoxypyrimidine (20 g, 112 mmol) and (1R,3s,5S)-tert-butyl 3-(methylamino)-9-azabicyclo[3.3.1]nonane-9-carboxylate (36.9 g, 145 mmol) in THF (300 mL) was added DIPEA (39.0 mL, 223 mmol) and the reaction mixture was stirred at 20-25° C. overnight. Additional (1R,3s,5S)-tert-butyl 3-(methylamino)-9-azabicyclo[3.3.1]nonane-9-carboxylate (4.26 g, 16.76 mmol) was added and the reaction mixture was warmed to 55° C., stirred for 2.5 h, cooled to RT and stirred for 2 d. Heptane (400 mL) was added over 30 min and the reaction mixture was filtered. The liquid phase was azeotroped with IPA (300 mL, then 200 mL) to about 200-300 mL, stirred at 5° C. overnight, and filtered to give the title intermediate (29.2 g, 71.4 mmol, 63.9% yield). HPLC Method A Retention time 28.27 min.

(c) tert-butyl (1R,3s,5S)-3-((4-methoxy-6-((5-(((triisopropylsilyl)oxy)methyl)-1H-pyrazol-3-yl)amino)pyrimidin-2-yl)(methyl)amino)-9-azabicyclo[3.3.1]nonane-9-carboxylate (7')

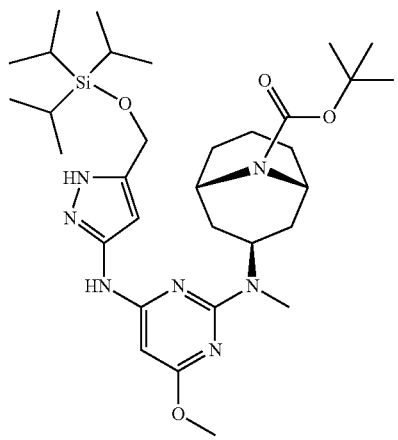

To a 250 mL flask were added the product of the previous step (9') (8 g, 20.16 mmol), the product of step (a) (3') (6.79 g, 25.2 mmol), $Cs_2CO_3$ (13.13 g, 40.3 mmol), Xphos Pd G2 (0.793 g, 1.008 mmol) and XPhos (0.480 g, 1.008 mmol), the reaction mixture was degassed three times and 1,4-dioxane (80 mL) and water (8.00 mL) were added to give a suspension. The reaction mixture was degassed three times under vacuum and nitrogen and heated to 100° C., refluxed overnight, and cooled to 35° C. SiliaMetS® thiol functionalized silica (4 g) was added and the reaction mixture was warmed to 65° C., stirred for 2 h, cooled to 50° C. and filtered through Celite® (5 g). Water (200 mL) and isopropyl acetate (200 mL) were added, the layers were separated, and the organic layer was washed with 20% $NaHSO_3$. The layers were separated and the organic layer was washed with brine. The layers were again separated and the aqueous layer was extracted with EtOAc (300 mL). Combined organic layers were dried over $Na_2SO_4$ and evaporated to provide crude product (about 20 g). Methanol (50 mL) was added and the reaction mixture was stirred at RT, filtered and washed with methanol (10 mL) to remove solid to give the title compound as a methanol solution which was used directly in the next step. HPLC Method A: Retention time 16.05 min.

(d) (3-((2-(((1R,3s,5S)-9-azabicyclo[3.3.1]nonan-3-yl)(methyl)amino)-6-methoxypyrimidin-4-yl)amino)-1H-pyrazol-5-yl)methanol (1)

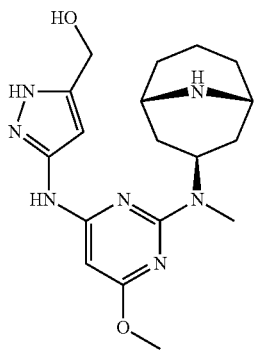

To a 250 mL flask were added the crude product of the previous step (7') in methanol (50 mL) (12.68 g, 20.136 mmol) and 3 M HCl in CPME (67.1 mL, 201 mmol) and the reaction mixture was stirred at RT for 2 h, and filtered to give the crude 3 HCl salt of the title compound (4.8 g, 9.94 mmol, 49.4% yield).

To a flask was added the above crude 3 HCl salt (2 g, 4.14 mmol) followed by water (30 mL) and SiliaMetS thiol functionalized silica 40% w/w (0.8 g, 4.14 mmol) and the reaction mixture was warmed to 65° C., stirred for 16 h, filtered through Celite and washed with water (1.5 mL). Acetone (120 mL) was added and the reaction mixture was stirred at RT overnight, filtered, washed with acetone (10 mL) and dried in vacuo at 50° C. to provide the purified 3 HCl salt of title compound (1.05 g, 2.175 mmol, 52.5% yield). HPLC Method A: Retention time 10.09 min.

(e) 1-(((1R,3s,5S)-3-((4-((5-(Hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile To a vial were added the product of the previous step (1) (0.83 g, 1.719 mmol) and NMP (8.3 mL), followed by TEA (1.44 mL, 10.31 mmol). The reaction mixture was stirred for 5-10 min. 3-Cyanoazetidine-1-sulfonyl chloride (0.466 g, 2.58 mmol) was added at 22° C. After 2 h, water (25 mL) was added over 30 min and the reaction mixture was stirred for 22 h. The reaction mixture was filtered and washed with water (2 mL) to give the title product (0.9 g, 1.704 mmol, 99% yield) as a white solid. HPLC Method A: Retention time 16.18 min.

Example 11: Crystalline 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile Form I To a 100 mL flask was added 1-(((1R,3s,5S)-3-((4-((3-(hydroxymethyl)-1H-pyrazol-5-yl)amino)-6-methoxypyrimidin-2-yl)(methyl)amino)-9-azabicyclo[3.3.1]nonan-9-yl)sulfonyl)azetidine-3-carbonitrile (1 g, 1.932 mmol) and DMF (3.00 mL) followed by acetone (4 mL). Water (6 mL) was then added over 5 min and the reaction mixture was stirred overnight and filtered, and the solid was washed with water and acetone, and dried for 30 min to provide the title compound (0.94 g, 1.816 mmol, 94% yield). HPLC Method A: Retention time 16.30 min.

Example 12: Crystalline 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile Form I To a 20 L flask were added (3-((2-(((1R,3s,5S)-9-azabicyclo[3.3.1]nonan-3-yl)(methyl)amino)-6-methoxypyrimidin-4-yl)amino)-1H-pyrazol-5-yl)methanol (1) (1.20 kg, 2.69 mol), NMP (4.8 kg) and TEA (1.36 kg, 13.45 mol) and the reaction mixture was stirred at RT for 2 h. Next, NMP (2.4 kg) was added and the reaction mixture was stirred and cooled to 5-10° C. over about 1 h. 3-Cyanoazetidine-1-sulfonyl chloride (0.58 kg, 3.23 mol) was added in three batches, added every 0.5 h and the reaction mixture was stirred for 2 h and warmed to RT. Methanol (4.2 kg) was added, the reaction mixture was stirred for 0.5 h. Water (21.6 kg) was added over 3 h and the reaction mixture was stirred for 0.5 h and filtered. The solid was rinsed with methanol (1.0 kg) to give the crude title compound (1.33 kg) of which 1.20 kg was dissolved in NMP (3.6 kg). Acetone (3.8 kg) was added, the solution was filtered and the filtrate was heated to 45-55° C. with stirring. Water (6.6 kg) was added over 6 h and the mixture was stirred, cooled to 25-30° C. and filtered. The solid was rinsed with 4:5.5 acetone:water (1.5 L) and dried to provide the title compound (1.21 kg, 99% purity, 85% yield) HPLC Method B: Retention time 15.23 min. The product was micronized using an air jet milling process to the following particle size distribution: $X_{10}$=0.70 μm, $X_{50}$=2.17 μm, and $X_{90}$=6.15 μm, where $X_n$ is defined as the percentage of particles smaller than n %.

Example 13: Crystalline 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile Form II To a flask were added 1-(((1R,3s,5S)-3-((4-((5-(Hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile (16 g, 30.9 mmol) and DMF (160 mL) and the reaction mixture was filtered. To the solution was added water (480 mL) over 30 min and the reaction mixture was warmed to 65° C., stirred overnight, cooled to RT, stirred for 20 h, and filtered. The solid was dried overnight to give the title intermediate (11.8 g, 22.80 mmol, 73.8% yield). HPLC Method A: Retention time 16.19 min.

Examples 14-16: Properties of the Solid Forms of the Invention

Samples of the Form I and Form II crystalline freebase of 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile of Examples 12 and 13 respectively, were analyzed by powder X-ray diffraction (PXRD), differential scanning calorimetry (DSC), thermogravimetric analysis (TGA), and dynamic moisture sorption (DMS).

Example 14 Powder X-Ray Diffraction

The powder X-ray diffraction patterns of FIGS. 1 and 5 were obtained with a Bruker D8-Advance X-ray diffractometer using Cu-Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 35° in 2θ with a step size of 0.02° and a scan speed of 0.30° seconds per step. The data acquisition was controlled by Bruker DiffracSuite measurement software and analyzed by Jade software (version 7.5.1). The instrument was calibrated with a corundum standard, within ±0.02° two-theta angle. Observed PXRD 2θ peak positions and d-spacings are shown in Tables 4 and 5, respectively for crystalline Form I and crystalline Form II. The two-theta peak positions of the Form I micronized material listed in Table 4, were compared with peak positions of an unmicronized sample prepared by the same synthetic process. The maximum difference observed in two-theta peak positions was 0.04 degrees.

TABLE 4

PXRD Data for Crystalline Form I

| 2-Theta | d(Å) | Area | A % |
|---|---|---|---|
| 8.89 | 9.94 | 460823 | 100 |
| 10.64 | 8.31 | 75783 | 16.4 |
| 10.99 | 8.05 | 116893 | 25.4 |
| 12.99 | 6.81 | 153914 | 33.4 |
| 13.44 | 6.59 | 156394 | 33.9 |
| 14.54 | 6.09 | 66952 | 14.5 |
| 14.76 | 6.00 | 85164 | 18.5 |
| 15.02 | 5.89 | 133090 | 28.9 |
| 15.74 | 5.63 | 59537 | 12.9 |
| 16.25 | 5.45 | 75492 | 16.4 |
| 16.47 | 5.38 | 85726 | 18.6 |
| 20.16 | 4.40 | 443759 | 96.3 |
| 20.39 | 4.35 | 207159 | 45.0 |
| 20.93 | 4.24 | 66277 | 14.4 |
| 21.81 | 4.07 | 52296 | 11.3 |
| 22.22 | 4.00 | 79031 | 17.1 |
| 23.36 | 3.81 | 62926 | 13.7 |
| 23.56 | 3.77 | 92923 | 20.2 |
| 24.99 | 3.56 | 70165 | 15.2 |
| 25.27 | 3.52 | 124788 | 27.1 |
| 26.25 | 3.39 | 98075 | 21.3 |
| 26.84 | 3.32 | 77303 | 16.8 |

TABLE 5

PXRD Data for the Crystalline Form II

| 2-Theta | d(Å) | Area | A % |
|---|---|---|---|
| 8.87 | 9.96 | 342177 | 100 |
| 10.64 | 8.31 | 61376 | 17.9 |
| 11.01 | 8.03 | 86511 | 25.3 |
| 12.88 | 6.87 | 105843 | 30.9 |
| 13.47 | 6.57 | 107366 | 31.4 |
| 14.51 | 6.10 | 45973 | 13.4 |
| 14.72 | 6.01 | 45739 | 13.4 |
| 15.04 | 5.88 | 77441 | 22.6 |
| 15.58 | 5.69 | 32094 | 9.4 |
| 16.51 | 5.36 | 48996 | 14.3 |
| 16.88 | 5.25 | 18790 | 5.5 |
| 19.02 | 4.66 | 23117 | 6.8 |
| 20.00 | 4.44 | 190640 | 55.7 |
| 20.42 | 4.35 | 63067 | 18.4 |
| 20.73 | 4.28 | 56902 | 16.6 |
| 21.67 | 4.10 | 26834 | 7.8 |
| 22.30 | 3.98 | 47801 | 14 |
| 22.93 | 3.87 | 20999 | 6.1 |
| 23.32 | 3.81 | 40192 | 11.7 |
| 25.28 | 3.52 | 57929 | 16.9 |
| 25.99 | 3.43 | 28870 | 8.4 |

Example 15: Thermal Analysis

Figure 2:
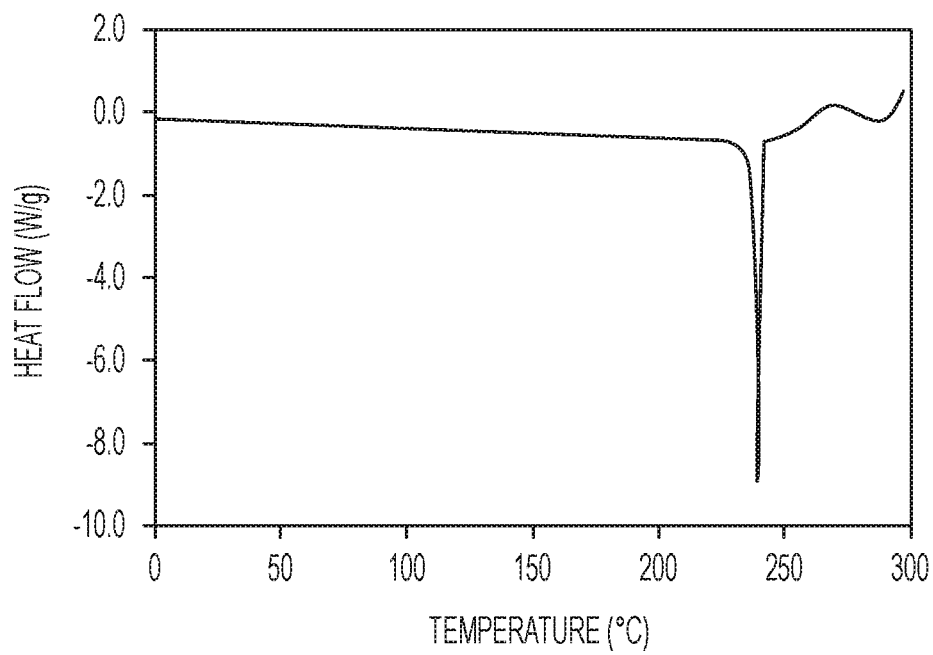
FIG. 2 shows a differential scanning calorimetry (DSC) thermogram of crystalline Form I.
Figure 6:
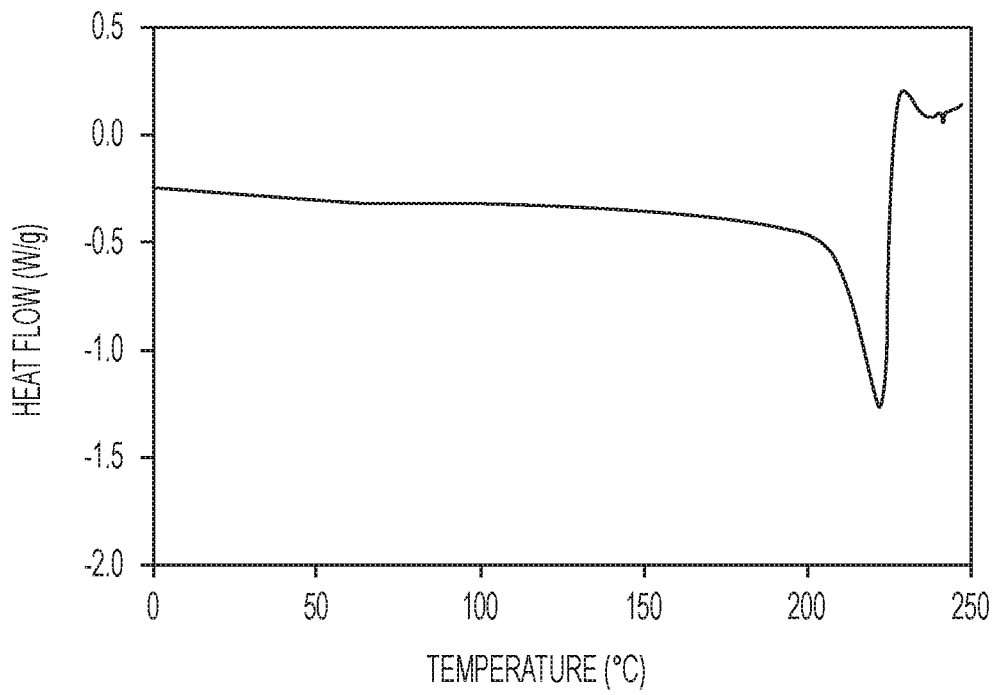
FIG. 6 shows a differential scanning calorimetry (DSC) thermogram of crystalline Form II.

Differential scanning calorimetry (DSC) was performed using a TA Instruments Model Q-100 module with a Thermal Analyst controller. Data were collected and analyzed using TA Instruments Thermal Analysis software. A sample of each crystalline form was accurately weighed into a covered aluminum pan. After a 5 minute isothermal equilibration period at 5° C., the sample was heated using a linear heating ramp of 10° C./min from 0° C. to 300° C. A representative DSC thermogram of the Form I and Form II crystalline freebase of the invention is shown in FIGS. 2 and 6, respectively.

Figure 3:
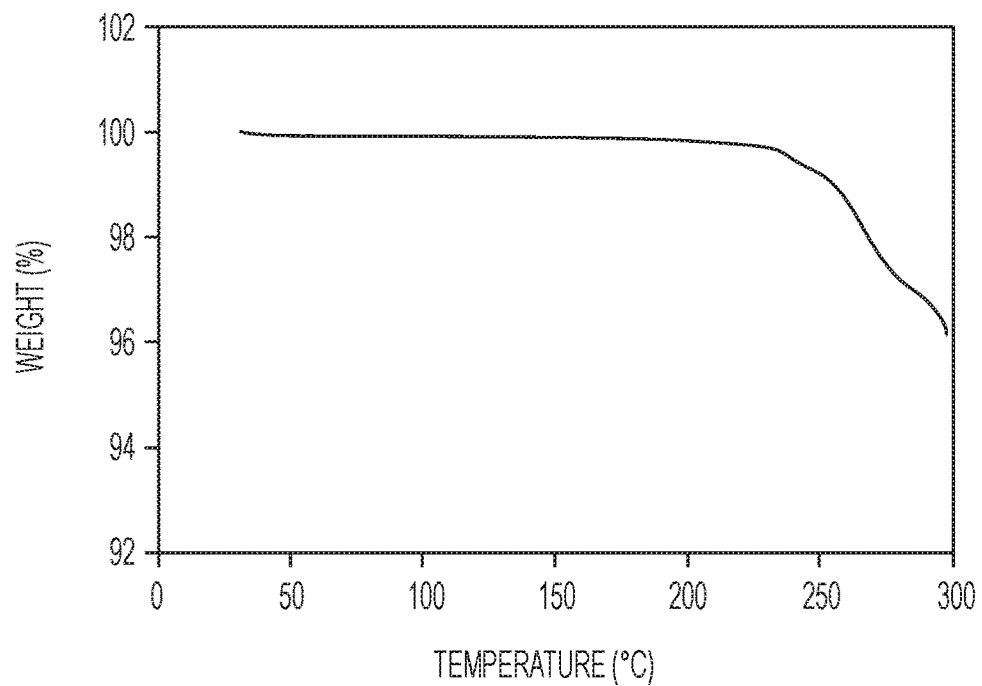
FIG. 3 shows a thermal gravimetric analysis (TGA) plot of crystalline Form I.
Figure 7:
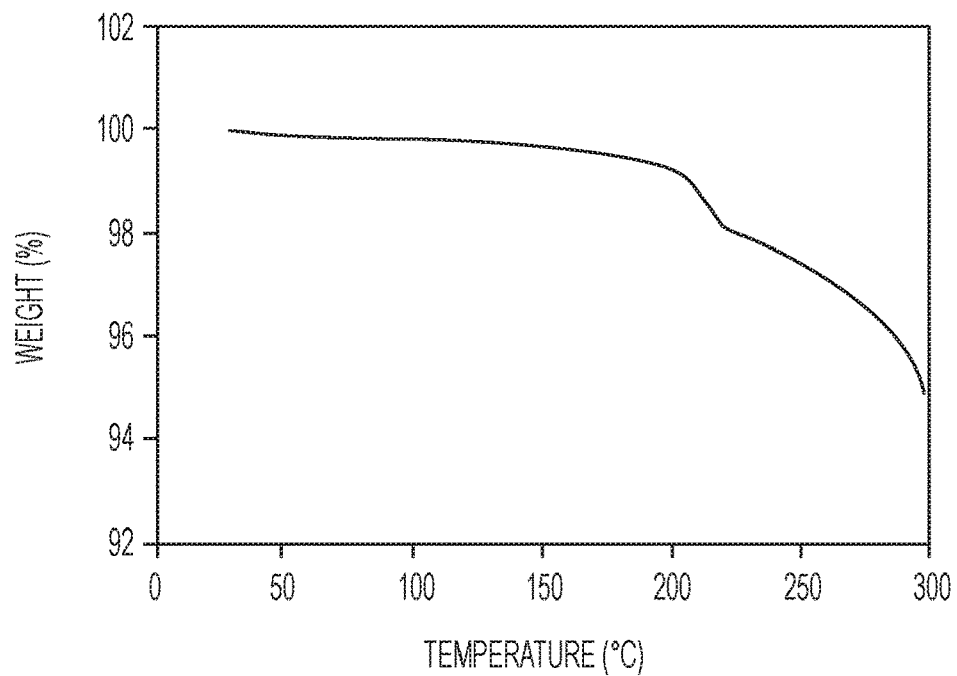
FIG. 7 shows a thermal gravimetric analysis (TGA) plot of crystalline Form II.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 300° C. The balance and furnace chambers were purged with nitrogen flow during use. A representative TGA trace of the Form I and Form II crystalline freebase of the invention is shown in FIGS. 3 and 7.

Example 16: Dynamic Moisture Sorption Assessment

Figure 4:
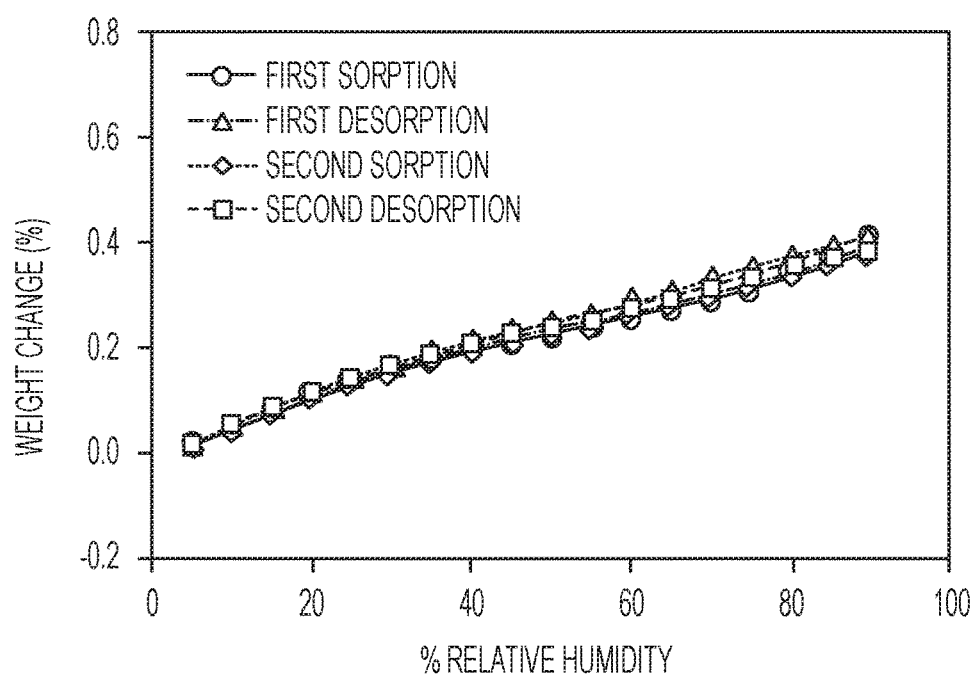
FIG. 4 shows a dynamic moisture sorption (DMS) isotherm of crystalline Form I observed at a temperature of about 25° C.
Figure 8:
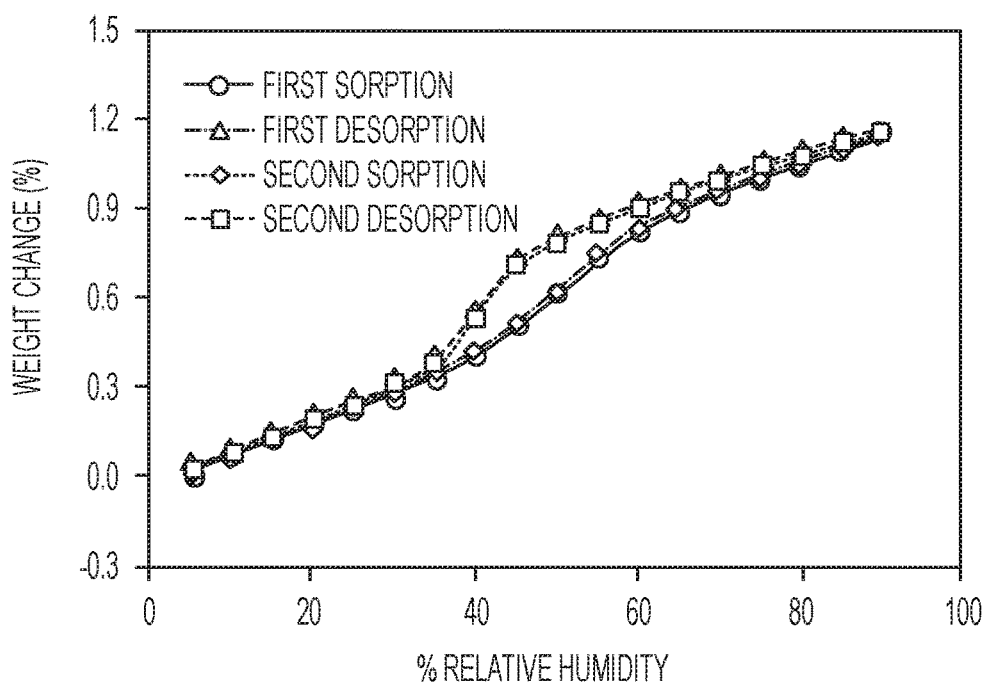
FIG. 8 shows a dynamic moisture sorption (DMS) isotherm of crystalline Form II observed at a temperature of about 25° C.

Dynamic moisture sorption (DMS) measurement was performed using a VTI atmospheric microbalance, SGA-100 system (VTI Corp., Hialeah, Fla. 33016). A weighed sample was used and the humidity was lowest possible value (close to 0% RH) at the start of the analysis. The DMS analysis consisted of an initial drying step (0% RH) for 120 minutes, followed by two cycles of sorption and desorption with a scan rate of 5% RH/step over the humidity range of 5% RH to 90% RH. The DMS run was performed isothermally at 25° C. A representative DMS trace for the Form I and Form II crystalline freebase of the invention is shown in FIGS. 4 and 8, respectively.

Biological Assays

The compounds of the invention have been characterized in one or more of the following biological assays.

Assay 1: Biochemical JAK and Off-Target Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM MgCl$_2$, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 μl total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 µM, 3 µM, 1.6 µM, and 10 µM; while the substrate concentration is 200 nM for all four assays. Kinase reactions were allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to pKi (negative logarithm of dissociation constant, Ki) using the Cheng-Prusoff equation.

Test compounds having a higher pKi value in each of the four JAK assays show greater inhibition of JAK activity. Compounds of the invention tested in this assay typically exhibited pKi values between about 7.5 and about 10.3.

A panel of off-target tyrosine kinase assays (ABL1, Flt3, RET, FGFR2, NTRK1, and pDGFRβ) were developed using a similar methodology, with recombinant enzymes obtained from Life Technologies and biotinylated peptide substrates synthesized at AnaSpec. All assays were carried out at ambient temperature with a final ATP concentration of 100 µM. Detection reagents, including Eu-anti-phosphotyrosine (pY20) antibody and SureLight APC-SA, were purchased from Perkin Elmer. Emission ratio signals (665 nm/615 nm) were recorded and utilized for data analysis, and the final results were expressed as $pIC_{50}$. Selected compounds tested in this assay typically exhibited $pIC_{50}$ values between about 5 and about 6.5.

Assay 2: Cellular JAK Potency Assay: Inhibition of IL-13

The potency of test compounds for inhibition of the JAK-dependent cytokine interleuken-13 (IL-13) was assessed by measuring IL-13 (IL-13, R&D Systems) induced STAT6 phosphorylation in HT-29 human colorectal adenocarcinoma cells (ATCC).

The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

HT-29 cells were grown at 37° C. in a 5% $CO_2$ humidified incubator in McCoy's 5a Modified medium (ATCC) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 25 µL medium, and were allowed to adhere overnight in the incubator. On day 2 of the assay, the medium was removed and replaced with 12 µL of assay buffer (Hank's Balanced Salt Solution/HBSS, 25 mM HEPES, and 1 mg/ml bovine serum albumin/BSA) containing dose-responses of test compounds. Compounds were serially diluted in DMSO and then diluted another 1000-fold in media to bring the final DMSO concentration to 0.1%. Cells were incubated with test compounds at 37° C. for 1 h, and followed by the addition of 12 µl of pre-warmed IL-13 (12 ng/ml in assay buffer) for stimulation. After incubating at 37° C. for 30 min, the assay buffer (containing compound and IL-13) was removed, and 10 µl of cell lysis buffer (25 mM HEPES, 0.1% SDS, 1% NP-40, 5 mM $MgCl_2$, 1.3 mM EDTA, 1 mM EGTA, and supplement with Complete Ultra mini protease inhibitors and PhosSTOP from Roche Diagnostics). The plates were shaken at ambient temperature for 30 min before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software. Results were expressed as the negative logarithm of the $IC_{50}$ value, $pIC_{50}$.

Test compounds having a higher $pIC_{50}$ value in this assay show greater inhibition of IL-13 induced STAT6 phosphorylation. Compounds of the invention tested in this assay typically exhibited $pIC_{50}$ values between about 6.0 and about 7.8.

Assay 3: JAK Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 500 cells/well density in white 384-well tissue culture plates (Corning) with 25 µL medium, and were allowed to adhere overnight in the incubator. On day 2 of the assay, 5 µL of medium containing dose-responses of test compounds was added, and incubated at 37° C. for 48 h. 30 µL of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as CC 15. Results were expressed as the negative logarithm of the $CC_{15}$ value, $pCC_{15}$.

It is expected that test compounds exhibiting a lower $pCC_{15}$ value in this assay have less likelihood to cause cytotoxicity. Compounds of the invention tested in this assay typically exhibited $pCC_{15}$ values between less than 5 and about 6.

In Vitro Assay Results

All of the compounds of Examples 1 to 9 and Tables 1 to 3 were tested in one or more of the assays described above. Since the JAK1 enzyme potency was found and understood to be predictive of the cellular potency described in Assay 2, enzyme characterization of certain compounds was limited to the JAK1 enzyme.

In Table 6 below, for the JAK1, JAK 2, JAK3, and TYK2 enzyme assays, A represents a $pK_i$ value ≥10 ($K_i$≤0.1 nM), B represents a $pK_i$ value between 9 and 10 ($K_i$ between 1 nM and 0.1 nM), C represents a $pK_i$ value between 8 and 9 ($K_i$ between 10 nM and 1 nM), and D represents a $pK_i$ value between 7.5 and 8 ($K_i$ between 31.6 nM and 10 nM). For the THP-1 potency assay, A represents a $pIC_{50}$ value ≥7.5

($IC_{50} \leq 32$ nM), B represents a $pIC_{50}$ value between 6.7 and 7.5 ($IC_{50}$ between 200 nM and 32 nM), and C represents a $pIC_{50}$ value between 6 and 6.7 ($IC_{50}$ between 1 µM and 200 nM).

TABLE 6

| Example Number | JAK 1 (pKi) | JAK 2 (pKi) | JAK 3 (pKi) | Tyk 2 (pKi) | HT-29 ($pIC_{50}$) |
|---|---|---|---|---|---|
| 1 | A | A | C | B | B |
| 2 | A | A | B | B | B |
| 3 | B | A | C | B | B |
| 4 | B | A | C | B | B |
| 5 | B | B | D | C | C |
| 6 | B | | | | |
| 7 | A | A | B | B | B |
| 8 | B | B | C | B | B |
| 9 | B | B | D | B | B |
| Table 1 | | | | | |
| 1-1 | C | | | | B |
| 1-2 | B | | | | C |
| 1-3 | C | | | | C |
| 1-4 | D | | | | |
| 1-5 | B | | | | B |
| 1-6 | A | | | | B |
| 1-7 | B | | | | |
| 1-8 | A | | | | A |
| 1-9 | B | | | | B |
| 1-10 | B | | | | |
| 1-11 | B | | | | B |
| 1-12 | B | B | C | B | |
| 1-13 | A | A | B | B | A |
| 1-14 | B | A | C | B | A |
| 1-15 | B | A | C | B | B |
| 1-16 | B | B | C | B | B |
| 1-17 | B | A | C | B | A |
| 1-18 | B | | | | |
| 1-19 | B | | | | A |
| Table 2 | | | | | |
| 2-1 | C | | | | C |
| 2-2 | B | | | | B |
| 2-3 | B | | | | B |
| 2-4 | B | | | | B |
| 2-5 | B | B | D | C | |
| 2-6 | B | B | C | B | |
| 2-7 | B | | | | B |
| 2-8 | B | | | | B |
| Table 3 | | | | | |
| 3-1 | B | | | | |
| 3-2 | B | B | | B | |
| 3-3 | B | B | | C | |
| 3-4 | B | B | | B | |
| 3-5 | B | B | | B | |
| 3-6 | B | B | | C | |
| 3-7 | B | B | | B | |
| 3-8 | B | B | | B | |

Assay 4: Cellular JAK Potency Assay: Inhibition of IL-4 Stimulated pSTAT6 in CD3+ T Cells The potency of test compounds for inhibition of interleukin-4 (IL-4) stimulated STAT6 phosphorylation was measured in CD3-positive (CD3+) T cells in human peripheral blood mononuclear cells (PBMCs) isolated from human whole blood (Stanford Blood Center) using flow cytometry. Because IL-4 signals through JAK, this assay provides a measure of JAK cellular potency.

CD3+ T cells were identified using a phycoerythrobilin (PE) conjugated anti-CD3 antibody (Clone UCHT1, BD Biosciences), while an Alexa Fluor 647 conjugated anti-pSTAT6 antibody (pY641, Clone 18/P, BD Biosciences) was used to detect STAT6 phosphorylation.

Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Heat Inactivated Fetal Bovine Serum (FBS, Life Technologies), 2 mM Glutamax (Life Technologies), 25 mM HEPES (Life Technologies) and 1× Pen/Strep (Life Technologies). Cells were seeded at 250,000 cells/well in media (200 µL), cultured for 1 h, and then resuspended in assay media (50 µL) (RPMI supplemented with 0.1% bovine serum albumin (Sigma), 2 mM Glutamax, 25 mM HEPES and 1× Penstrep) containing various concentrations of test compounds. Compounds were serially diluted in DMSO and then diluted another 500-fold (to a 2× final assay concentration) in assay media. Test compounds (50 µL) were incubated with cells at 37° C., 5% $CO_2$ for 1 h, followed by the addition of 50 µL of IL-4 (R&D Systems; final concentration 20 ng/mL) in pre-warmed assay media for 30 min. After cytokine stimulation, cells were fixed with pre-warmed fix solution (100 µL) (BD Biosciences) for 10 min at 37° C., 5% $CO_2$, washed twice with FACS buffer (1 mL) (2% FBS in DPBS), and resuspended in 1000 µL of ice cold Perm Buffer III (BD Biosciences) for 30 min at 4° C. Cells were washed twice with FACS buffer, and then resuspended in 100 µL of FACS buffer containing anti-CD3 PE (1:50 dilution) and anti-pSTAT6 Alexa Fluor 647 (1:5 dilution) for 60 min at room temperature in the dark. After incubation, cells were washed twice in FACS buffer before being analyzed using a LSRII flow cytometer (BD Biosciences).

To determine the inhibitory potency of test compounds in response to IL-4, the median fluorescent intensity (MFI) of pSTAT6 was measured in $CD_3$+ T cells. $IC_{50}$ values were determined from analysis of the inhibition curves of MFI vs compound concentration. Data are expressed as $pIC_{50}$ (negative decadic logarithm $IC_{50}$) values (mean±standard deviation). The compound of Example 2 exhibited a $pIC_{50}$ value of about 7.3 in this assay.

Assay 5: Cellular JAK Potency Assay: Inhibition of IFNγ-Induced pSTAT1 The potency of test compounds for inhibition of interferon gamma (IFNγ) stimulated STAT1 phosphorylation was measured in CD14-positive (CD14+) monocytes derived from human whole blood (Stanford Blood Center) using flow cytometry. Because IFNγ signals through JAK, this assay provides a measure of JAK cellular potency.

Monocytes were identified using a fluorescein isothiocyanate (FITC) conjugated anti-CD14 antibody (Clone RM052, Beckman Coulter), and an Alexa Fluor 647 conjugated anti-pSTAT1 antibody (pY701, Clone 4a, BD Biosciences) was used to detect STAT1 phosphorylation.

Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Fetal Bovine Serum (FBS, Life Technologies), 2 mM Glutamax (Life Technologies), 25 mM HEPES (Life Technologies) and 1× Pen/Strep (Life Technologies). Cells were seeded at 250,000 cells/well in media (200 µL), cultured for 2 h and resuspended in assay media (50 µL) (RPMI supplemented with 0.1% bovine serum albumin (Sigma), 2 mM Glutamax, 25 mM HEPES and 1× Penstrep) containing various concentrations of test compounds. Compounds were serially diluted in DMSO and then diluted another 1000-fold in media to bring the final DMSO concentration to 0.1%. Test compounds were incubated with cells at 37° C., 5% $CO_2$ for 1 h, followed by the addition of pre-warmed IFNγ (R&D Systems) in media (50 µL) at a final concentration of 0.6 ng/mL for 30 min. After cytokine stimulation, cells were fixed with pre-warmed fix solution (100 µL) (BD Biosciences) for 10 min at 37° C., 5% $CO_2$, washed twice with FACS buffer (1 mL) (1% BSA in PBS), resuspended in 1:10 anti-CD14 FITC:FACS buffer (100 µL), and incubated at 4° C. for 15 min. Cells were washed once, and then resuspended in ice cold Perm Buffer III (BD Biosciences) (100 µL) for 30 min at 4° C. Cells were washed twice with FACS buffer, and then resuspended in 1:10 anti-pSTAT1 Alexa Fluor 647:FACS buffer (100 µL) for 30 min at RT in the dark, washed twice in FACS buffer, and analyzed using a LSRII flow cytometer (BD Biosciences).

To determine the inhibitory potency of test compounds, the median fluorescent intensity (MFI) of pSTAT1 was measured in CD14+ monocytes. $IC_{50}$ values were determined from analysis of the inhibition curves of MFI vs compound concentration. Data are expressed as $pIC_{50}$ (negative decadic logarithm $IC_{50}$) values (mean±standard deviation). The compound of Example 2 exhibited a $pIC_{50}$ value of about 7.6 in this assay.

Assay 6: Determination of Absorption in Cannulated Rats

Oral bioavailability (F %), fraction absorbed ($F_a$%) and fraction escaping hepatic clearance ($F_h$%) were determined in Sprague Dawley rats from the following two studies:

(1) Pharmacokinetics in rats following an IV dose of test compound: Following IV dose, plasma samples were typically collected from 0-6 hr. Drug levels were determined using an LC-MS-MS method. The resulting drug levels were used to compute the IV pharmacokinetic parameters: AUC IV and Dose IV.

(2) Rats that have been cannulated in their portal vein (PV) and also in their jugular vein (JV) were dosed orally with test compound. Following oral dosing, plasma samples were typically collected from 0-6 hr from both the portal vein and the jugular vein. Drug levels were determined using an LC-MS-MS method. The resulting drug levels were used to compute the following pharmacokinetic parameters: AUC PO PV, AUC PO JV, and Dose PO.

Using data derived from the above studies, the oral bioavailability F %, and the quantities $F_a$% and $F_h$% were calculated from the following formulas:

$$F\% = (AUC\ PO\ JV/AUC\ IV)*(Dose\ IV/Dose\ PO)*100$$

$$F_a\% = (AUC\ PO\ PV/AUC\ IV)*(Dose\ IV/Dose\ PO)*100$$

$$F_h\% = AUC\ PO\ JV/AUC\ PO\ PV$$

where:
AUC PO JV=Area under the curve following oral dose and plasma collected from the jugular vein
AUC PO PV=Area under the curve following oral dose and plasma collected from the portal vein
AUC IV=Area under the curve following an intravenous dose
Dose IV=Intravenous Dose in mg/kg
Dose PO=Oral Dose in mg/kg The compounds of Examples 1-4 were tested in this assay and exhibited oral bioavailability (F %) less than about 25%. In particular, the compounds of Examples 1, 2, and 4 exhibited F % values less than about 5%. In addition, the compounds of Examples 1 and 2 exhibited absorption at the portal vein ($F_a$%) less than about 25% while the compounds of Examples 3 and 4 exhibited $F_a$% values greater than 40%.

Assay 7: Colon Pharmacokinetics in Rats

The test compound was formulated in 0.5% methylcellulose in water and dosed via oral gavage at 3.2 mg/kg and 100 mg/kg to Sprague Dawley rats. At various time points (typically 0.5, 1, 3, 6, 24 hr) post dosing, blood samples were removed via cardiac puncture and intact colons were excised from the rats. Blood samples were centrifuged at 1500×g for 15 min to collect plasma. Colons were washed with ice cold phosphate buffered saline (PBS), weighed, and homogenized at a dilution of 1:10 in PBS. Plasma and colon levels of test compound were determined by LC-MS analysis against analytical standards constructed into a standard curve in the test matrix. A colon to plasma ratio was determined as the ratio of the colon AUC to the plasma AUC in µg hr/g. The compound of Example 2 exhibited a colon to plasma ratio in excess of about 250 at 5 mg/kg and in excess of about 1200 at 100 mg/kg.

Assay 8: Mouse Model of Oxazalone-Induced Colitis

Oxazolone-induced colitis is an experimental model that has a histological resemblance to human ulcerative colitis (Heller et al. *Immunology*, 2002, 17, 629-638). Adult BALB/C mice from Harlan were used in the assay. On day 1, animals were lightly anesthetized with isoflurane and the hairs between the shoulder were carefully removed before oxazolone (4%, 150 µL, 4:1 acetone: olive oil formulation) or vehicle solution was slowly applied for skin sensitization. Seven days after skin sensitization, the mice were fasted overnight, anesthetized with isoflurane inhalation, and a 1 mL syringe equipped with a 3.5-F catheter, filled with oxazolone solution, was inserted carefully about 4 cm into the colon of the mouse. Following insertion, 50 µL of the oxazolone solution (1%, 1:1 ethanol:water formulation) was injected very slowly (over 30 sec using an injection pump) into the colon. The catheter was removed and the mice were held vertically (head down) for 2 min to ensure that the entire oxazolone solution remained inside the colon. Drug treatment (PO, BID or TID) or vehicle was initiated a day prior to the oxazolone intrarectal (IR) challenge. Two-day post oxazolone intrarectal challenge, the Disease Activity Index (DAI) was assessed by treatment-blinded experimenters for each mouse according to the criteria score: stool consistency score (0, normal; 2, loose; 4, diarrhea), gross bleeding score (0, absence; 2, blood tinged; 4, presence), and weight loss score (0, none; 1, 1%-5%; 2, 5%-10%; 3, 10%-20%; 4, more than 20%); DAI=average of (stool consistency score+gross bleeding score+weight loss score).

Selected compounds of the invention were tested in the assay. Efficacy in the model is evidenced by a decrease in DAI score as compared with the score from vehicle treated animals. The compounds of examples 2 and 4 exhibited a statistically significant decrease in DAI score as compared with vehicle treated animals in the oxazalone model at a dose of 1, 3, and/or 10 mg/kg BID, while the compound of example 1 did not exhibit a statistically significant decrease at the doses up to 10 mg/kg BID tested in the assay.

Assay 9: Immunosuppression Effects in Mouse Splenic Natural Killer (NK) Cells

Depletion of mouse splenic cells is an experimental model of immunosuppression (Kudlacz et al., *Am. J. of Transplantation*, 2004, 4, 51-57). The compound of Example 2 was assessed in the mouse splenic cell model following the same treatment paradigm as that used in the oxazolone-induced colitis model (Assay 8).

Adult male Balb/C mice (12-14 weeks of age) from Harlan were used for the study. The compound (1, 10 and 100 mg/kg, BID) and tofacitinib (30 and 60 mg/kg, BID) as a positive control were dosed orally for three days to naïve mice. Spleens were harvested 1 h post last dose and crushed immediately for cell subtype staining. Prior to fixation, fluorophore-labelled antibodies for CD19 (FITC; B cells), CD3e (PE; pan T cells) and DX5 (APC; NK cells) were incubated with splenocyte samples from each animal to allow for simultaneous, multiple subtype % analysis on the flow cytometer. The number of total spleen cells for each animal was measured by Scepter™ 2.0 Handheld Automated Cell Counter.

The absolute number of lymphocyte subtype population (e.g., splenic B, T and NK cells) was calculated from the percentage of each subtype times total spleen cells for each animal. A one way ANOVA, with Dunnett's post hoc test, was used to compare the splenic lymphocytes number of the vehicle and test compound groups. The a level was set at p<0.05. Data were presented as the mean±SEM for each group.

The positive control, tofacitinib (30 and 60 mg/kg; PO, BID), dose-dependently and significantly decreased splenic NK cell counts. In the same study, splenic NK cell counts were unaffected by the compound of Example 2 at PO (BID) doses up to 100 mg/kg (the maximum dose tested). No treatment effect was observed for the B and T cell populations with either compound.

This data, in conjunction with the 1 mg/kg minimal dose that caused a significant anti-colitic effect in the mouse model of oxazolone-induced colitis (Assay 8), allow a functional therapeutic index of >100 to be computed for the compound of Example 2.

Assay 10: Dermal Pharmacokinetics in Mouse and Mini-Pig Skin

The objective of this assay was to determine the epidermal, dermal and plasma pharmacokinetics of a test compound following a 24 hr exposure to intact mouse or mini-pig skin.

The compound prepared in Example 12, 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile, was formulated to 0.5% (w/w) in cream or ointment as described, as Formulation A or Formulation B, respectively in Table 7.

Twenty-four hours prior to dosing the hair was shaved from the back of 25 g male Balb/c mice exposing an area at of least 6 cm$^2$ (about 10% of body surface) and, in a separate experiment, of 10 kg Gottingen mini-pigs exposing an area of at least 450 cm$^2$ (about 10% of body surface). At time zero, following isoflurane anesthesia, the test compound was applied to the back of mice or mini-pigs at a dose of 25 µL/cm$^2$. The skin was covered with an adhesive cover to prevent loss of compound to the cage or bedding.

Following 24 h exposure, the backs were gently washed with soap and water to remove non-absorbed drug and patted dry. Immediately following this washing, blood was drawn by cardiac puncture from the mice and via venipuncture from the mini-pigs. The outer skin (stratum corneum) was then removed by adhesive tape stripping. Upon exposure of the epidermis a 0.5 cm punch biopsy was taken. The epidermis and dermis were quickly separated, weighed and snap frozen. Similar samples were obtained at 48 h post dosing in mice and at 48 h, 94 h, and 168 h (7 days) post-dosing in mini-pigs.

Epidermis and dermis samples were homogenized in 1:10 (w/v) water using a Covaris ultrasonic homogenizer. Samples were extracted in 3 volumes of acetonitrile and quantified against a standard curve via LC-MS analysis. As evidenced by the pharmacokinetic parameters AUC$_{0-t}$ for plasma, epidermis and dermis shown in Table 8 below, significant compound exposure was exhibited in epidermis and dermis layers while the plasma exposure was negligible in mice and below the limit of quantitation in mini-pig.

TABLE 7

| Formulation A | | Formulation B | |
|---|---|---|---|
| Compound of Example 12 | 0.5% | Compound of Example 12 | 0.5% |
| Stearic Acid | 5% | Octylhydroxystearate | 5% |
| Cetostearyl Alcohol | 5% | C8-C10 Triglyceride | 5% |
| Isopropyl Palmitate | 4% | Vaseline (Petrolatum) | 79.5% |
| Octylhydroxystearate | 2% | N-Methylpyrrolidine | 10% |
| BRIJ S2 (PEG 2 Stearyl Ether) | 1.08% | | |
| BRIJ S20 (PEG 20 Stearyl Ether) | 6.92% | | |
| N-Methylpyrrolidine | 10% | | |
| PEG400 | 10% | | |
| RO Water | 55.5% | | |

TABLE 8

| | Plasma AUC$_{0-t}$ (µg*hr/mL) | Epidermis AUC$_{0-t}$ (µg*hr/g) | Dermis AUC$_{0-t}$ (µg*hr/g) |
|---|---|---|---|
| Mouse Formulation A | 0.014 | 718 | 61 |
| Mouse Formulation B | 0.006 | 2830 | 296 |
| Mini-pig Formulation A | <0.001 | 988 | 71 |
| Mini-pig Formulation B | <0.001 | 4030 | 114 |

Assay 11: Topical Tpa-Induced Irritant Contact Dermatitis Model in Mice

The objective of this assay is to assess the anti-inflammatory effect in a model of acute dermatitis of test compounds being studied for cutaneous inflammatory conditions such as atopic dermatitis (Dong et al., *J Pharmacol Exp Ther*, 2013, 344, 436-446).

Topical dermal application of phorbol ester 12-O-tetradecanoylphorbol-13-acetate (TPA) in mice causes an inflammatory response that is characterized by edema and neutrophil influx at the early phase (2-24 h) and by epidermal cell proliferation at the later phase (24-48 h) (Griffiths et al., *Agents and Actions*, 1988, 25, 344-351). Female Balb/c mice were topically administered with either vehicle (1:7 DMSO:acetone) or 20 µL of a solution of TPA (2.5 µg) in vehicle on each ear. At 30 min before and 15 min after TPA administration, either vehicle or the compound of Example 2 at doses of 30, 100, 300, 1000, and 3000 µg in vehicle was applied topically to each ear. The degree of inflammation was assessed as the change in ear thickness at 6 hours after TPA application. The compound of Example 2 exhibited a dose- and concentration-dependent inhibition of TPA-induced increase in ear thickness. The maximum statistically significant effect was 41% inhibition observed at the 1000 µg dose.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A crystalline form of 1-(((1R,3s,5S)-3-((4-((5-(hydroxymethyl)-1H-pyrazol-3-yl)amino)-6-methoxypyrimidin-2-yl)(methyl)amino)-9-azabicyclo[3.3.1]nonan-9-yl)sulfonyl)azetidine-3-carbonitrile, wherein the crystalline form has a powder X-ray diffraction pattern comprising diffraction peaks at 2θ values of 8.89±0.20, 12.99±0.20, 13.44±0.20, and 20.16±0.20.

2. The crystalline form of claim 1 wherein the powder X-ray diffraction pattern has two or more additional diffraction peaks at 2θ values selected from 10.64±0.20, 10.99±0.20, 15.02±0.20, 15.74±0.20, 16.47±0.20, 20.93±0.20, 22.22±0.20, and 26.25±0.20.

3. The crystalline form of claim 1 wherein the crystalline form has a differential scanning calorimetry trace recorded at a heating rate of 10° C. per minute which shows a maximum in endothermic heat flow at a temperature between about 235° C. and about 245° C.

4. The crystalline form of claim 1 wherein the powder X-ray diffraction pattern has an additional diffraction peak at a 2θ value of 10.64±0.20.

5. The crystalline form of claim 4 wherein the powder X-ray diffraction pattern has an additional diffraction peak at a 2θ value of 15.02±0.20.

6. The crystalline form of claim 5 wherein the powder X-ray diffraction pattern has an additional diffraction peak at a 2θ value of 16.47±0.20.

* * * * *

UNITED STATES PATENT AND TRADEMARK OFFICE
CERTIFICATE OF CORRECTION

PATENT NO. : 10,485,803 B2  
APPLICATION NO. : 16/014233  
DATED : November 26, 2019  
INVENTOR(S) : Xiaojun Huang Page 1 of 1

It is certified that error appears in the above-identified patent and that said Letters Patent is hereby corrected as shown below:

In the Claims

At Column 57, Line 2, Claim 1:
"(1R,3s,5S)" should be "(1*R*,3*s*,5*S*)"

At Column 57, Line 3, Claim 1:
"-1H-pyrazol" should be "-1*H*-pyrazol"

At Column 57, Line 7, Claim 1:
"20" should be "2θ"

At Column 57, Line 11, Claim 2:
"20" should be "2θ"

Signed and Sealed this
Third Day of March, 2020

Andrei Iancu
*Director of the United States Patent and Trademark Office*